(12) United States Patent
Wang et al.

(10) Patent No.: US 9,952,442 B2
(45) Date of Patent: Apr. 24, 2018

(54) HIGH BRIGHTNESS SOLID STATE ILLUMINATION SYSTEM FOR FLUORESCENCE IMAGING AND ANALYSIS

(71) Applicant: Excelitas Canada, Inc., Vaudreuil-Dorion (CA)

(72) Inventors: Yong Wang, Markham (CA); Paul Constantinou, Burlington (CA); Sola Anne Kuk, Toronto (CA)

(73) Assignee: Excelitas Canada, Inc., Vaudreuil-Dorion (CA)

( * ) Notice: Subject to any disclaimer, the term of this patent is extended or adjusted under 35 U.S.C. 154(b) by 386 days.

(21) Appl. No.: 14/862,492

(22) Filed: Sep. 23, 2015

(65) Prior Publication Data
US 2016/0076735 A1    Mar. 17, 2016

Related U.S. Application Data

(63) Continuation-in-part of application No. 13/897,237, filed on May 17, 2013, now Pat. No. 9,239,133.

(51) Int. Cl.
*F21V 9/16* (2006.01)
*G01N 21/64* (2006.01)
(Continued)

(52) U.S. Cl.
CPC ....... *G02B 27/141* (2013.01); *G01N 21/6456* (2013.01); *G01N 2201/062* (2013.01); *H01S 5/005* (2013.01); *H01S 5/0071* (2013.01)

(58) Field of Classification Search
CPC ......... G01N 21/6456; G01N 2201/062; G02B 27/141; H01S 5/005; H01S 5/0071; F21K 9/00; F21Y 2115/10; F21Y 2115/30
See application file for complete search history.

(56) References Cited

U.S. PATENT DOCUMENTS

| 5,080,462 A | 1/1992 | Goto |
| 7,070,300 B2 | 7/2006 | Harbers et al. |

(Continued)

OTHER PUBLICATIONS

Yu, et al. "Luminous properties of color tunable strontuem thioselenide phosphors for LEDS application", Materials Letters 65 (2011) 2690-2692.

(Continued)

*Primary Examiner* — Peggy Neils
(74) *Attorney, Agent, or Firm* — Peter A. Nieves; Sheehan Phinney Bass & Green PA

(57) ABSTRACT

An illumination system includes a phosphor to emit light in a wavelength band $\Delta\lambda_{PHOSPHOR}$, a second light source to emit light at a second wavelength $\lambda_2$ within an absorption band of the phosphor, a third light source to emit light at a third wavelength $\lambda_3$ and a fourth light source to emit light at a fourth wavelength $\lambda_4$. A controller drives the second, third and fourth light sources. A first dichroic optical element: 1) directs light from the phosphor to an optical output of the system, 2) directs light from the third light source to the optical output, and 3) directs light from the fourth light source to the optical output. A second dichroic optical element: 1) directs light from the third light source to the first dichroic optical element, and 2) directs the light from the fourth light source to the first dichroic optical element.

34 Claims, 19 Drawing Sheets

(51) Int. Cl.
*H01S 5/00* (2006.01)
*G02B 27/14* (2006.01)

(56) References Cited

U.S. PATENT DOCUMENTS

| | | |
|---|---|---|
| 7,416,313 B2 | 8/2008 | Westphal et al. |
| 7,898,665 B2 | 3/2011 | Brukilacchio et al. |
| 8,029,439 B2 | 10/2011 | Todd et al. |
| 8,096,668 B2 | 1/2012 | Abu-Ageel |
| 8,203,784 B2 | 6/2012 | Nolte et al. |
| 8,292,434 B2 | 10/2012 | Horvarth et al. |
| 8,567,973 B2 | 10/2013 | Li et al. |
| 8,733,948 B2 * | 5/2014 | Ogawa .................. F21V 9/00 353/94 |
| 2006/0227570 A1 | 10/2006 | Rutherford et al. |
| 2008/0094835 A1 | 4/2008 | Marra et al. |
| 2009/0040523 A1 | 2/2009 | Brukilacchio |
| 2009/0052833 A1 | 2/2009 | Yang et al. |
| 2009/0190371 A1 | 7/2009 | Root et al. |
| 2011/0038138 A1 | 2/2011 | Cardullo et al. |
| 2011/0044046 A1 | 2/2011 | Abu-Ageel |
| 2011/0149549 A1 | 6/2011 | Miyake |
| 2012/0147329 A1 | 6/2012 | Papac et al. |
| 2012/0230007 A1 | 9/2012 | Kawakami |
| 2012/0230011 A1 | 9/2012 | Harada |
| 2013/0250544 A1 | 9/2013 | Zink et al. |
| 2013/0314893 A1 | 11/2013 | Paquette |
| 2014/0022512 A1 | 1/2014 | Li et al. |
| 2014/0340869 A1 | 11/2014 | Wang et al. |
| 2014/0355240 A1 | 12/2014 | Farchtchian |

OTHER PUBLICATIONS

Shin, et al. Luminescence characterization of $(Ca_{1-x}Sr_x)(S_{1-y}Se_y):Eu^{2+}$, $M_3$= (M=Sc and Y) for high color rending white LED, Materials Chemistry and Physics 126 (211) 591-595.

* cited by examiner

HIGH BRIGHTNESS SOLID STATE ILLUMINATION SYSTEM FOR FLUORESCENCE IMAGING AND ANALYSIS

CROSS-REFERENCE TO RELATED APPLICATIONS

This application is a continuation-in-part (CIP) of co-pending U.S. patent application Ser. No. 13/897,237, entitled High Brightness Solid States Illumination System for Fluorescence Imaging and Analysis, which was filed on May 17, 2013, which was related to co-pending U.S. patent application Ser. No. 13/900,089, filed May 22, 2013, entitled "High Brightness Illumination System and Wavelength Conversion Module for Microscopy and Other Applications", which claims priority from U.S. Provisional patent application, Ser. No. 61/651,130, filed May 24, 2012. Each of these prior applications is incorporated herein by reference in its entirety.

FIELD OF THE INVENTION

This invention relates to high brightness solid state illumination systems, particularly illumination systems for fluorescence imaging and analysis.

BACKGROUND

High radiance illumination sources are required for fluorescence imaging and analysis, including fluorescence microscopy. Some applications require broadband or white light illumination. Other applications require relatively narrow band illumination of a particular wavelength range in the ultraviolet (UV), visible or infrared (IR) spectral region.

For example, conventional microscopy illumination systems typically utilize short arc lamps such as high pressure mercury, metal halide, and xenon lamps. These lamps are capable of very high radiance and are suitable sources for direct coupled illumination systems, as well as light guide coupled illumination systems, e.g. using a liquid light guide or a fiber light guide. Nevertheless, it is recognized that there are a number of problems associated with conventional lamp technologies, such as short lifetime, temporal variation of the output power, high voltage operation (typically kilovolts are required to strike the lamp), and use of mercury. The latter is now seen as an environmental hazard and subject to regulations to limit use in numerous countries throughout the world.

Solid state light lighting technology has progressed significantly in recent years and some high brightness light sources using solid state Light Emitting Devices (LEDs), e.g. light emitting diodes, are now available that can potentially provide sufficiently high radiance, broadband illumination for replacement of conventional arc lamps. Solid state LED light sources can offer advantages over conventional arc lamps, such as, much improved lifetime, lower cost of ownership, lower voltage operation, lower power consumption (enabling some battery operated portable devices), and freedom from mercury. Additionally LED light sources can be readily controlled electronically, by modulating the current or voltage driving the device, which allows for fast switching and intensity control through the LED driver, which can be a significant advantage in many applications.

Nevertheless, despite technological advances in LED technology, high brightness LED light sources are not available to cover all wavelengths required for illumination systems for fluorescence imaging and analysis. In particular, the output of LED devices still do not match the radiance of traditional arc-lamps in some regions of the visible spectrum, especially in the 540 nm to 630 nm spectral band, i.e. in the green/yellow/amber range of the visible spectrum. The solid state lighting industry refers to this issue as the "green gap". Emission in this region of the spectrum is fundamentally limited by the lack of availability of semiconductor materials having a suitable band gap to produce light of the required wavelength.

This is a particular problem for fluorescence imaging and analysis which may, for example, require illumination of a biological sample with a relatively narrow band of illumination of a particular wavelength that is absorbed by a selected fluorophore or marker in the substance under test.

For example, a traditional fluorescence illumination system, e.g. for fluorescence imaging or microscopy, comprises a short arc mercury lamp which provides light emission having spectral peaks near 365 nm, 405 nm, 440 nm, 545 nm and 575 nm. Standard fluorophores that are commonly used for fluorescence imaging and analysis are selected to have absorption spectra having peaks optimized to match these lamp emission peaks. To replace a standard mercury lamp illuminator with a LED based illuminator, it is desirable to be able to provide emission at the same wavelengths and with a comparable output power. There are suitably powerful LEDs that are commercially available for emission at 365 nm, 405 nm, 440 nm. However, in view of the "green gap" mentioned above, there are currently no single color, high brightness LEDs commercially available for emission at 545 nm and 575 nm.

It is well known in the art of LED lighting and illumination to use LEDs in combination with luminescent materials, i.e. fluorescent materials or phosphors, to generate light of wavelengths that are outside the range emitted directly by the LEDS, i.e. by wavelength conversion. In particular, a UV or blue light emitting LED may be combined with a remote or direct die-contact phosphor layer or coating to obtain broadband light emission of a desired color temperature. For example, a blue light emitting diode or diode array with an emission peak in the range between 445 nm and 475 nm is combined with a phosphor layer comprising particles of Ce:YAG (cerium doped yttrium aluminum garnet) suspended in an encapsulant material such as silicone, which is deposited directly on the LED. The blue light from the LED is absorbed by the phosphor and generates a broadband green/yellow/amber light which combines with the scattered blue light to produce a spectrum that provides the perception of white light. The overall brightness is limited by the blue light intensity from the LED and thermal quenching of the phosphor, and the spectrum provides limited emission in regions of the spectrum seen as green/yellow, approximately 560 nm and amber, approximately 590 nm.

Thus, relative to a mercury lamp, commercially available white light LEDs that use a blue light emitting LED combined with a Ce:YAG phosphor, produce significantly weaker emission in the 545 nm and 575 nm regions. For example, at the objective plane of a microscope, output power at 545 nm and 575 nm from such a white light LED was found to be about 10 times lower than the output power from a mercury lamp. This level of power is insufficient for most conventional fluorescence microscopy applications.

By increasing the drive current, some improvement of the light output can be achieved, but fundamentally, the power in this circumstance is limited by the maximum drive current density (i.e. current per unit area) and factors, such as, the LED optical to electrical conversion efficiency, the LED output intensity, the phosphor quantum efficiency, and thermal quenching of both the LED and phosphor, as well as the cooling capacity. Even in the best case, the output from an overdriven air cooled white LED is still 4 to 5 times less than a conventional lamp within the 545 nm and 575 nm spectral range and the lifetime may be significantly reduced by overdriving the device.

The following references provide some other examples of the use of LED sources combined with fluorescent materials or phosphors in other forms.

U.S. Pat. No. 7,898,665 to Brukilacchio et al., issued Mar. 1, 2011, entitled "Light Emitting Diode Illumination System," for example, discloses a system comprising an arrangement of multiple LEDS that are coupled to a fluorescent rod which emits at a different wavelength to provide sufficiently high brightness illumination for applications such as microscopy or endoscopy. For example a single crystal of Ce:YAG may be pumped by multiple LEDs to generate yellow or amber emission. However, the efficiency of such a device would be limited by total internal reflection due to the high index of refraction of Ce:YAG and requires coupling of multiple LEDs to generate output of sufficient brightness, which increases the cost, size, thermal and electrical requirements.

To provide a more compact and efficient system, the above referenced related copending U.S. Patent application No. 61/651,130, discloses an illumination system that comprises a laser light source, e.g. providing blue light emission in the 440 nm to 490 nm range, for excitation of a wavelength conversion module comprising a wavelength conversion medium, such as Ce:YAG crystal, of a particular shape and size, set in a mounting for thermal dissipation, and an optical concentrator. The shape and size of the wavelength conversion crystal, provides a compact light source with a configuration suitable for applications that require high brightness and narrow bandwidth illumination at a selected wavelength, e.g. for fluorescence microscopy, or other applications requiring étendue-limited coupling or light guide coupling. While effective, due to the particular shape and size of the crystal and cooling requirements, this system is currently relatively costly to manufacture. A solution that is lower cost, compact and provides a broader spectrum is desirable for some applications.

Thus, there is a need for improved or alternative high radiance illumination sources, particularly those that can provide illumination at wavelengths of 545 nm and 575 nm, for example, for fluorescence imaging and analysis applications.

SUMMARY OF THE INVENTION

The present invention seeks to overcome or mitigate one or more disadvantages of known high brightness illumination systems for fluorescence imaging and analysis, or at least provide an alternative.

Thus, one aspect of the present invention provides method of providing high brightness illumination for fluorescence imaging and analysis, comprising: providing a first light source comprising a light emitting device (LED) and a phosphor layer, the LED emitting a first wavelength $\lambda_1$ within an absorption band of the phosphor layer and the phosphor layer emitting broadband light emission of longer wavelength comprising light in a wavelength band $\Delta\lambda_{PHOSPHOR}$; providing a second light source comprising a laser emitting a second wavelength $\lambda_2$ within the absorption band of the phosphor layer; and while operating the LED to generate emission at $\lambda_1$ and $\Delta\lambda_{PHOSPHOR}$, concurrently optically pumping the phosphor layer with laser emission $\lambda_2$ to increase emission intensity in the phosphor emission wavelength band $\Delta\lambda_{PHOSPHOR}$. In some implementations, the phosphor layer is optically pumped by the LED or the laser, but not concurrently by both.

The method may comprise optically coupling emission comprising $\lambda_1$ and $\Delta\lambda_{PHOSPHOR}$, along a common optical axis, to an optical output. The method may comprise providing another light source emitting another wavelength $\lambda_3$, and optically coupling emission comprising $\lambda_1$, $\Delta\lambda_{PHOSPHOR}$ and $\lambda_3$, along a common optical axis, to an optical output.

By way of example, the LED light source may comprise a standard white light emitting LED light source, i.e. comprising a blue light emitting LED emitting at wavelength $\lambda_1$ and a yellow Ce:YAG phosphor layer or coating providing broadband emission over a wavelength band $\Delta\lambda_{PHOSPHOR}$. Typically, during normal operation of the blue light emitting LED, the phosphor layer is not saturated by light from the blue LED. Thus, concurrent optical pumping of the phosphor layer with the laser wavelength $\lambda_2$, within the absorption band of the Ce:YAG phosphor layer, effectively increases the phosphor emission $\Delta\lambda_{PHOSPHOR}$ in the green, yellow and amber regions of the spectrum.

In particular, the supplementary laser optical pumping of the phosphor provides increased optical output over the emission band of the phosphor, so that sufficiently high radiance can be achieved at specific wavelengths, e.g. 545 nm and 575 nm, which are conventionally used for fluorescence imaging and analysis applications.

Another aspect of the present invention provides an illumination system for fluorescence imaging and analysis, comprising: a light source module comprising: a first light source comprising a first light emitting device (LED) and a phosphor layer, the first LED for providing emission at a first wavelength $\lambda_1$ within an absorption band of the phosphor layer and the phosphor layer providing broadband light emission of longer wavelength comprising light in a wavelength band $\Delta\lambda_{PHOSPHOR}$; a second light source for providing laser emission at a second wavelength $\lambda_2$, within the absorption band of the phosphor layer; a controller for driving the first light source to generate emission at $\lambda_1$ and $\Delta\lambda_{PHOSPHOR}$ and for concurrently driving the laser and optically pumping the phosphor layer with the laser wavelength $\lambda_2$, to increase emission in the emission band of the phosphor $\Delta\lambda_{PHOSPHOR}$; and optical coupling means for coupling light emission to an optical output of the illumination system.

Thus a laser pumped LED light source unit or module is provided, which has a high radiance output in the emission band of the phosphor $\Delta\lambda_{PHOSPHOR}$. The pump laser wavelength $\lambda_2$ may be the same as the LED wavelength $\lambda_1$, or different from $\lambda_1$, provided it is within the absorption band of the phosphor layer. The laser is preferably a solid state laser, e.g. a laser diode, and the control unit provides LED/laser controllers and LED/laser drivers. A suitable choice of phosphor allows for an optical output with high brightness at particular wavelengths, e.g. for applications such as fluorescence imaging and analysis. The phosphor layer may be selected to cover a band within the spectral range from 350 nm to 750 nm and more particularly from 530 nm to 630 nm, i.e. within in the green gap.

In particular, this system provides for high brightness (i.e. high radiance) illumination, e.g., in the 545 nm and 575 nm bands, which are commonly used for fluorescence imaging and analysis, such as, for fluorescence microscopy and for array slide scanners.

The optical coupling means comprises one or more optical elements such as lenses or optical concentrators for focusing the laser emission onto the phosphor layer, collecting emission at $\lambda_1$ and $\Delta\lambda_{PHOSPHOR}$, and coupling the emission at these wavelengths to the optical output of the light source module.

For example, the optical coupling means comprises an optical element for coupling the laser wavelength $\lambda_2$ to the phosphor layer for optical pumping of the phosphor layer and for coupling emission from the first LED and the phosphor layer, comprising $\lambda_1$ and $\Delta\lambda_{PHOSPHOR}$, to the optical output. Preferably the optical element comprises a dichroic element that acts as a beam-splitter/combiner for coupling the laser wavelength $\lambda_2$ onto the phosphor layer for optical pumping of the phosphor layer and for coupling emission from the first LED and the phosphor layer, comprising $\lambda_1$ and $\Delta\lambda_{PHOSPHOR}$, to the optical output.

If the pump laser wavelength $\lambda_2$ is less than the wavelength emission $\lambda_1$ of the LED, in a preferred embodiment, the dichroic element has a band edge $\lambda_D$ greater than the laser wavelength $\lambda_2$, so that it reflects the laser emission $\lambda_2$ and transmits output light emission comprising $\lambda_1$ and $\Delta\lambda_{PHOSPHOR}$.

As an example, $\lambda_1$ comprises emission in the range from 445 nm to 475 nm, i.e. from a blue LED, and $\Delta\lambda_{PHOSPHOR}$ covers the emission wavelength range from 500 nm to 750 nm. Preferably $\Delta\lambda_{PHOSPHOR}$ covers the emission wavelength range from at least 530 to 630 nm (i.e. the "green gap"), and the pump laser wavelength $\lambda_2$ is 450 nm or less.

A dichroic beam-splitter/combiner, having a band edge wavelength $\lambda_D$, between $\lambda_1$ and $\lambda_2$, may be positioned for reflecting the laser emission $\lambda_2$ and transmitting output light emission comprising $\lambda_1$ and $\Delta\lambda_{PHOSPHOR}$. For example, for wavelength ranges in the example above, if the pump laser wavelength $\lambda_2$ is 440 nm, and the blue LED emits $\lambda_1$ in the range from 445 nm to 475 nm, the dichroic element has a band edge $\lambda_D$ of 443 nm.

The illumination system may further comprise one or more additional light sources, e.g. at least one of a LED light source providing an emission wavelength $\lambda_3$ and an LED light source providing emission at wavelength $\lambda_4$. For example, these additional LED light sources are individual LED light sources that provide outputs $\lambda_3$ and $\lambda_4$ in the near UV and UV spectral regions, respectively. Optical coupling elements are provided to couple outputs at these and other wavelengths, along a common optical axis, to the optical output of the system.

Optical coupling elements may include a second dichroic element, i.e. a dichroic beam-splitter/combiner, for combining outputs $\lambda_3$ and $\lambda_4$, and then the first dichroic element combines $\lambda_3$ and $\lambda_4$ with $\lambda_1$ and $\Delta\lambda_{PHOSPHOR}$. For example, the first LED has an emission band $\lambda_1$ in the range between 440 nm and 490 nm and more preferably between 445 nm and 475 nm. The $\Delta\lambda_{PHOSPHOR}$ band emitted by the phosphor layer is in the range from 500 nm to 750 nm and more preferably in the range from 530 nm to 630 nm. If the phosphor layer is Ce:YAG as described above, the laser wavelength $\lambda_1$ is preferably 450 nm or less, for optical pumping of the phosphor layer. The additional individual LED light sources provide $\lambda_3$ comprising near UV emission in the range from 410 nm to 445 nm and $\lambda_4$ comprising UV emission in the range from 370 nm to 410 nm or from 350 nm to 390 nm.

In this example, a second dichroic element having a band pass edge wavelength between $\lambda_3$ and $\lambda_4$, e.g. 409 nm, is used to combine these two wavelengths. Then, if the laser pump wavelength $\lambda_2$, and LED emission at $\lambda_3$ and $\lambda_4$, are all on the short wavelength side of the 443 nm band edge wavelength $\lambda_D$ of the first dichroic element, this element combines $\lambda_3$ and $\lambda_4$ with $\lambda_1$ and $\Delta\lambda_{PHOSPHOR}$, along the primary optical axis, to provide an optical output comprising each of these wavelengths.

Optionally the system may comprise one or more additional individual LED light sources and/or one or more additional light source modules for light emission in other spectral bands. For example, additional light sources may provide spectral bands that are in the ultraviolet and near ultraviolet region. These additional sources may comprise, e.g.: a UV LED emitting in the range from 350 nm to 390 nm, e.g. having a peak at 365 nm; or a UV LED emitting in the range from 370 to 410 nm, e.g. having a peak at 385 nm; or a phosphor coated UV LED emitting in the near UV range from 410 nm to 445 nm.

In one embodiment, the at least one additional light source or light source module comprises a LED providing emission at $\lambda_4$ and a phosphor layer (Phosphor2) providing a broad emission band $\Delta\lambda_{PHOSPHOR2}$. For example, if both $\lambda_4$ and $\Delta\lambda_{PHOSPHOR2}$ lie on the same side (i.e. the short wavelength side in the example above) of the band edge wavelength $\lambda_D$ of the first dichroic element, the dichroic element combines $\lambda_4$ and $\Delta\lambda_{PHOSPHOR2}$ with $\lambda_1$ and $\Delta\lambda_{PHOSPHOR}$, to enable coupling of each of these wavelength bands, along the primary optical axis, to the optical output of the light source unit.

Typically, an optical filtering system within a fluorescence imaging system, such as a fluorescence microscope, provides for further filtering of a selected wavelength band from the output of the illumination system.

If desired, the illumination system may also comprise one or more additional LED light source modules, providing other wavelength bands. It may comprise an additional laser pumped LED light source module, i.e. a second pump laser emitting a wavelength $\lambda_5$ within an absorption band of a second phosphor layer (Phosphor2), for optically pumping the second phosphor layer (Phosphor2). A second dichroic beam-splitter/combiner may be provided, having a wavelength edge that is selected to reflect the laser wavelength $\lambda_5$ and transmit the emission bands at $\lambda_4$ and $\Delta\lambda_{PHOSPHOR2}$.

Another aspect of the present invention provides illumination system for fluorescence imaging and analysis, comprising: first and second light source modules and a controller;

the first light source module for providing emission in a first wavelength band, comprising: a first light source comprising a first LED and a first phosphor layer, the first LED providing emission at a first wavelength $\lambda_1$ within an absorption band of the phosphor layer and the first phosphor layer providing broadband light emission $\Delta\lambda_{PHOSPHOR1}$; a second light source comprising a laser emitting at a second wavelength $\lambda_2$, within the absorption band of the first phosphor layer; wherein the controller concurrently drives the first light source to generate emission comprising $\lambda_1$ and $\Delta\lambda_{PHOSPHOR1}$ and drives the laser for optically pumping the first phosphor layer with the laser wavelength $\lambda_2$ to increase emission in the emission band of the phosphor $\Delta\lambda_{PHOSPHOR1}$;

the second module for providing emission in a second wavelength band different from the first wavelength band, comprising: a third light source comprising second LED and a second phosphor layer different from the first phosphor layer, the second LED emitting at a wavelength $\lambda_4$ within an absorption band of the second phosphor layer and the second phosphor layer providing broadband light emission $\Delta\lambda_{PHOSPHOR2}$; a fourth light source comprising a laser emitting at a wavelength $\lambda_5$ within the absorption band of the second phosphor layer; wherein the controller concurrently drives the second light source to generate emission comprising $\lambda_4$ and $\Delta\lambda_{PHOSPHOR2}$ and the laser for optically pumping the second phosphor layer with the laser wavelength $\lambda_5$ and the laser wavelength $\lambda_5$, to increase emission in the emission band of the second phosphor $\Delta\lambda_{PHOSPHOR2}$; and optical coupling means comprising at least one dichroic beam-splitter/combiner for coupling one or more of $\lambda_1$, $\Delta\lambda_{PHOSPHOR1}$, $\lambda_4$ and $\Delta\lambda_{PHOSPHOR2}$, along a common optical axis, to an optical output of the illumination system.

The optical coupling means comprises optical coupling elements such as a coupling lens, an optical concentrator or other optics, and one or more dichroic elements having suitable passband, i.e. dichroic beam-splitters/combiners, to enable the LED light sources and laser light sources to be compactly arranged and for optically coupling the light emission from the LEDs and the phosphor layers to the primary optical axis, aligned to the optical output of the illumination system. The optical coupling elements may comprise dichroic elements for splitting and/or combining emission wavelengths from each light source, as required, and preferably first and second dichroic beam-splitters/combiners having band edges selected for reflecting laser wavelengths $\lambda_2$ and $\lambda_5$, respectively.

An illumination system, according to preferred embodiments of the invention, has the potential of meeting and exceeding the output of the best arc lamps systems available today at particular wavelengths used for fluorescence microscopy, while overcoming at least some of the limitations of existing high brightness LED light sources.

The foregoing and other objects, features, aspects and advantages of the present invention will become more apparent from the following detailed description, taken in conjunction with the accompanying drawings, of preferred embodiments of the invention, which description is by way of example only.

BRIEF DESCRIPTION OF DRAWINGS

In the drawings, identical or corresponding elements in the different Figures have the same reference numeral, or corresponding elements have reference numerals incremented by 100 in successive Figures.

DESCRIPTION OF PREFERRED EMBODIMENTS

Figure 1:
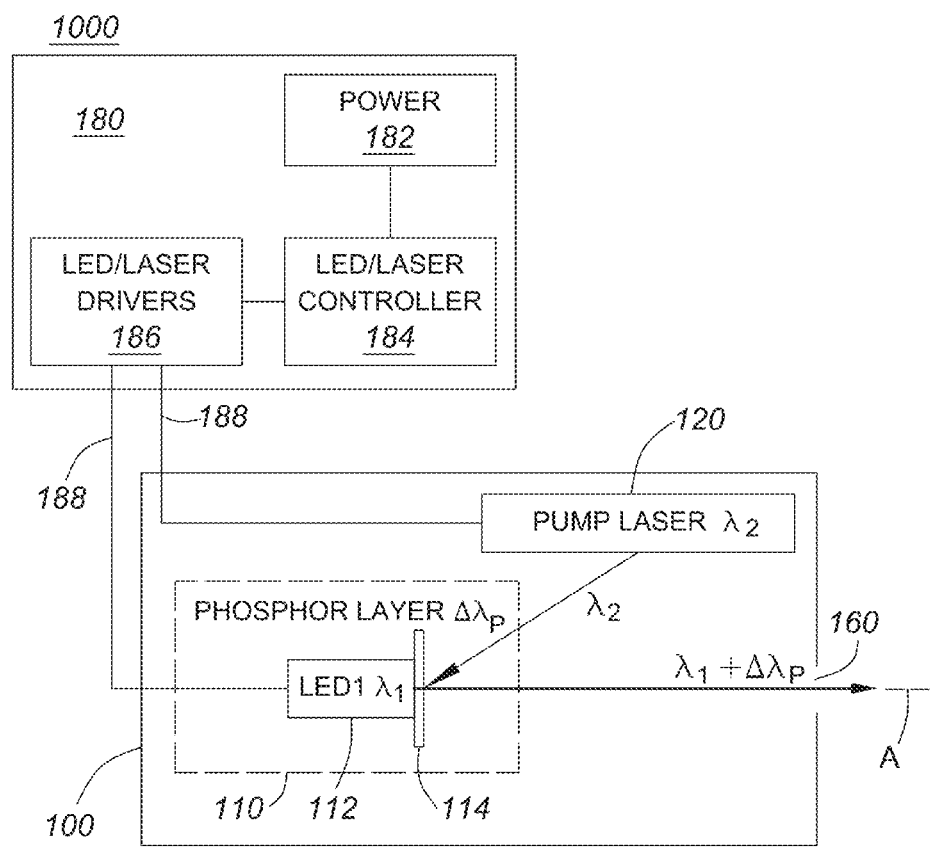
FIG. 1 illustrates schematically an illumination system comprising a light source module according to a first embodiment of the invention.

A schematic diagram showing elements of an illumination system 1000, according to a first embodiment of the invention, is shown in FIG. 1. The illumination system 1000 comprises a light source unit or module 100 for providing high brightness illumination for fluorescence illumination and analysis. The light source unit 100 comprises first and second light sources 110 and 120. The first light source 110 comprises an LED 112 (LED1) and a phosphor layer 114, the LED 112 emitting a first wavelength $\lambda_1$ within an absorption band of the phosphor layer and the phosphor layer 114 emitting broadband light emission of longer wavelength, comprising light in a wavelength band $\Delta\lambda_{PHOSPHOR}$ (abbreviated as $\Delta\lambda_P$ in the Figures). The second light source 120 comprises a laser 120 emitting at a second wavelength $\lambda_2$, also within an absorption band of the phosphor layer. The illumination system 1000 also comprises drive means or drive unit, i.e. controller/driver 180 comprising a power supply 182, LED/laser controller 184 and LED/laser drivers 186, which are coupled by electrical connections 188 for concurrently driving the LED 110 and the laser 120, to enable optical pumping of the phosphor layer 114 with the laser 120, i.e. at the laser wavelength $\lambda_2$.

As shown in FIG. 1, in a simple arrangement to provide for laser pumping of the phosphor layer, the first and second light sources 110 and 120 are arranged so that the laser 120 illuminates the phosphor layer 114 at an angle, e.g. at grazing incidence, and emission from the LED 112 and the phosphor 114, comprising wavelengths $\lambda_1$ and $\Delta\lambda_{PHOSPHOR}$, that is emitted along a primary optical axis A, is coupled to an optical output 160 of the system. The laser 120 may be coupled to the phosphor layer through a light guide, an optical concentrator or other optical elements (not shown in FIG. 1).

The first light source 110 may be a phosphor coated LED, mounted on a suitable heatsink for thermal management, e.g. a phosphor LED which provides high brightness white light illumination, i.e. comprising a blue light emitting LED 112 having a deposited phosphor coating 114 providing emission over a desired wavelength band $\Delta\lambda_{PHOSPHOR}$ in the longer wavelength visible range. Under normal operation of the first light source 110, even when the LED 112 is driven at higher current or voltage (i.e. the maximum driving current is limited by a maximum driving current density), the phosphor layer 114 is not saturated by the blue light emission from LED 112. Thus, supplementary optical pumping of the phosphor 114, using the pump laser 120, significantly increases the optical output of the phosphor emission band $\Delta\lambda_{PHOSPHOR}$. The pump laser wavelength $\lambda_2$ may be the same or different from the LED wavelength $\lambda_1$, provided it is also within the absorption band of the phosphor layer 114.

Thus, under normal operation, without laser pumping, driving the LED 112 generates light from the LED itself at wavelength $\lambda_1$ together with emission in the emission band of the phosphor $\Delta\lambda_{PHOSPHOR}$. By concurrently optically pumping the phosphor with the laser wavelength $\lambda_2$, the optical output in the emission band of the phosphor $\Delta\lambda_{PHOSPHOR}$ is increased significantly, as will be further explained below with reference to FIGS. 2, 3 and 4, and subsequent Figures.

A preferred arrangement for high brightness illumination systems for fluorescence imaging and analysis, comprises two or more light source modules, i.e. providing different output wavelengths, and optical elements for coupling outputs from the two or more light source modules along a primary optical axis to the optical output of the system.

Figure 2:
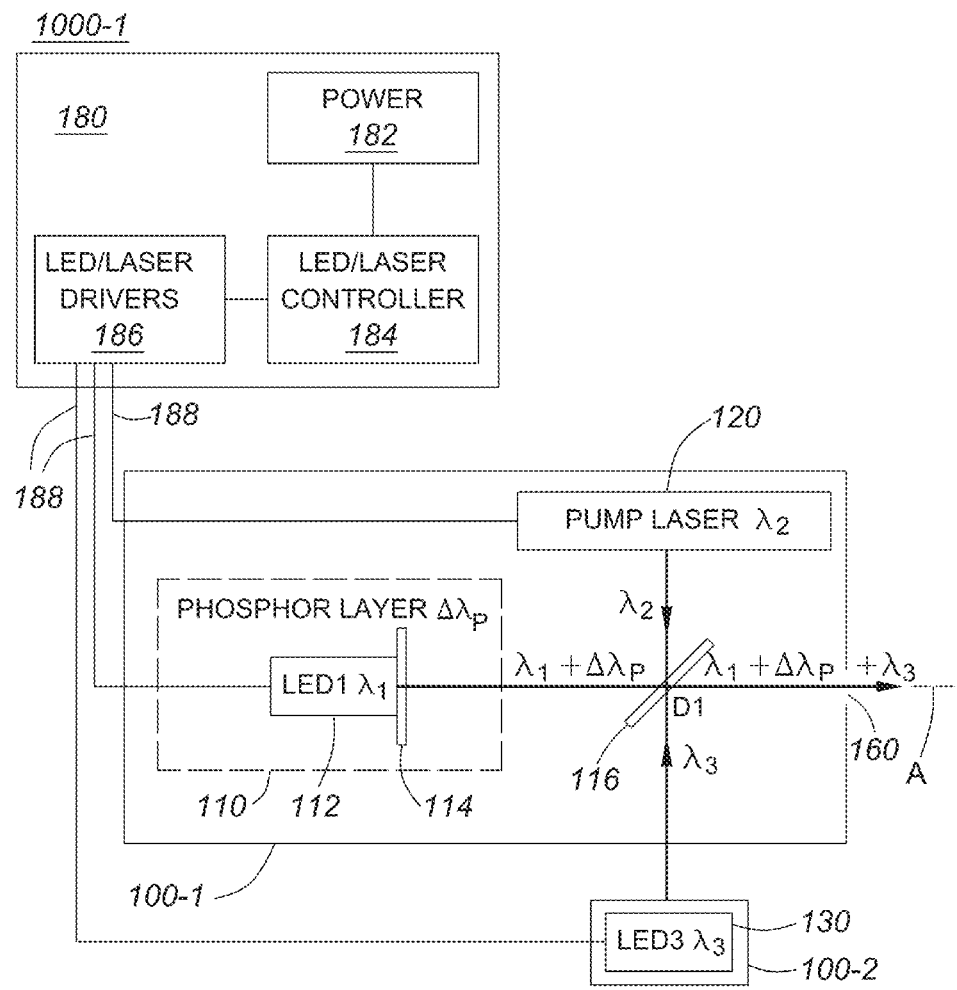
FIG. 2 illustrates schematically an illumination system comprising a light source module according to a second embodiment.

Thus, a schematic diagram showing elements of an illumination system 1000-1, according to a second embodiment of the invention, is shown in FIG. 2. The illumination system 1000-1 comprises a light source unit or module 100-1 for providing high brightness illumination for fluorescence illumination and analysis. The light source unit 100-1 is similar to that shown in FIG. 1, in that it comprises first and second light sources 110 and 120. The first light source 110 comprises an LED 112 (LED1) and a phosphor layer 114, the first LED 112 emitting at a first wavelength $\lambda_1$ within an absorption band of the phosphor layer and the phosphor layer 114 emitting broadband light emission of longer wavelength, comprising light in a wavelength band $\Delta\lambda_{PHOSPHOR}$ (abbreviated as $\Delta\lambda_P$ in the Figures). The second light source 120 comprises a laser 120, preferably a solid state laser diode, emitting at a second wavelength $\lambda_2$, also within an absorption band of the phosphor layer. Also provided is a dichroic element, i.e. a beam-splitter/combiner, 116 (D1), which reflects the laser wavelength $\lambda_2$ to couple the pump laser excitation to the phosphor layer, and transmits $\lambda_1$ and $\Delta\lambda_{PHOSPHOR}$. That is, for the arrangement shown in FIG. 2, the dichroic beam-splitter/combiner has a band edge $\lambda_D$ between $\lambda_1$ and $\lambda_2$. Thus the combined emission from the LED 112 and the phosphor 114, $\lambda_1$ and $\Delta\lambda_{PHOSPHOR}$, is coupled, along the primary optical axis A, to the optical output 160. Optionally, another light source 100-2, i.e. comprising an LED 130 (LED3) emitting another wavelength band $\lambda_3$ may be provided and the dichroic beam-splitter/combiner 116 is also used to couple $\lambda_3$ to the primary optical axis.

Figure 3:
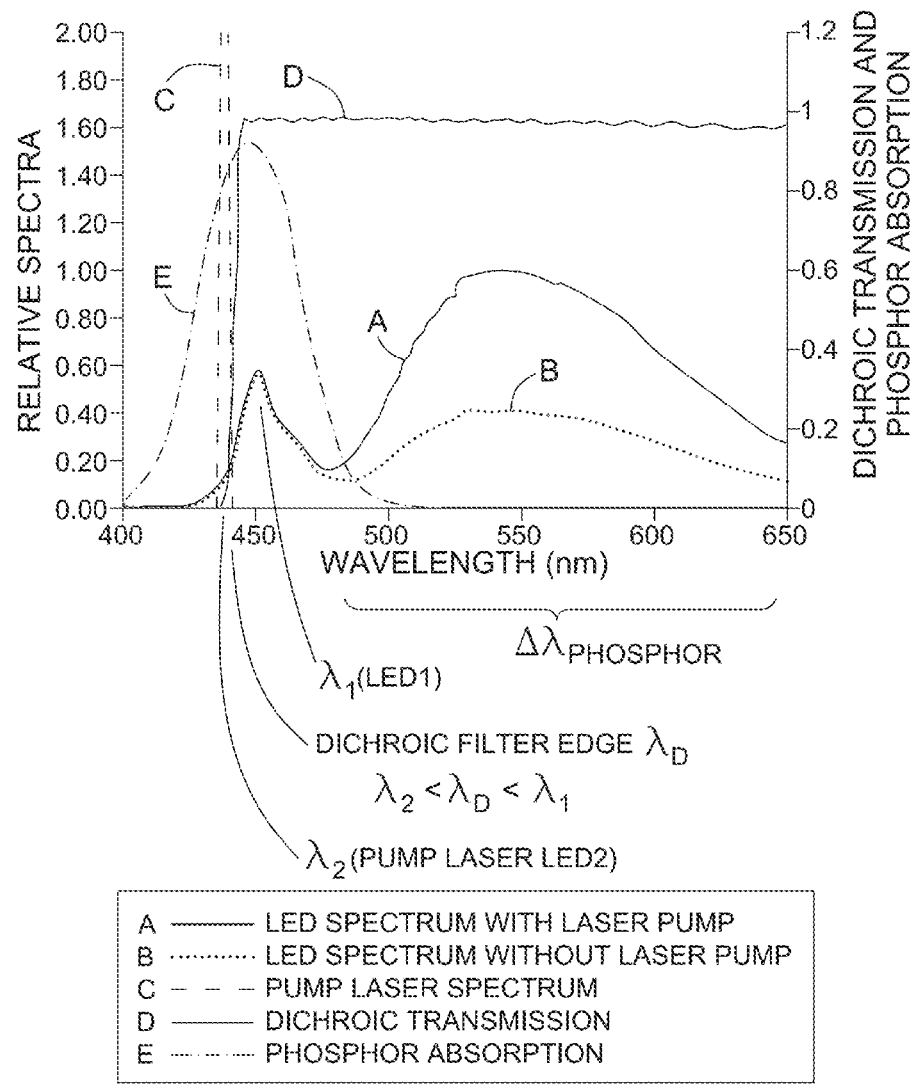
FIG. 3 shows spectral data for the light source module 100-1 illustrated in FIG. 2, without laser pumping and with laser pumping.

Preferably, other optical coupling elements such as lenses or optical concentrators are also provided for more efficiently coupling the laser emission $\lambda_2$ to the phosphor, and for collecting the light emission $\lambda_1+\Delta\lambda_{PHOSPHOR}$, and coupling this light emission, to an optical output 160 of the light source unit 100. However, for simplicity these additional optical elements are not shown in FIG. 2, and they will be described in more detail below with reference to FIGS. 11 to 14. By way of example only, the first light source 110 comprises, a low cost, commercially available "white light" solid state light source i.e. a "white light LED" comprising a phosphor layer 114 pumped by a blue light LED 112, which is manufactured for the demands of general high brightness lighting. One example is a PhlatLight® White LED manufactured by Luminus Devices, which comprises a blue light emitting LED and a Ce:YAG type phosphor coating that provides an emission spectrum, such as illustrated in FIG. 3, spectrum B. The spectrum comprises a strong blue light peak in a first spectral region $\lambda_1$ at around 450 nm from LED1 and a broad emission band $\Delta\lambda_{PHOSPHOR}$ from 500 nm to 700 nm at longer wavelengths that peaks in the 530 nm to 630 nm region of the spectrum. Thus under normal operation, i.e. when electrically driven at a suitable current and voltage, the resulting light emission, $\lambda_1$ and $\Delta\lambda_{PHOSPHOR}$, combines to provide a white light spectrum, spectrum B. With supplementary optical pumping by laser 120 at $\lambda_2$, i.e. at 440 nm as shown in spectrum C, in the absorption band of the phosphor (spectrum E), the laser pumped emission spectrum shows increased intensity in the broad emission band $\Delta\lambda_{PHOSPHOR}$ of the phosphor, as shown by spectrum A. That is, spectrum A comprises emission from LED1 at $\lambda_1$ at 445 nm to 475 nm, at a similar intensity as in spectrum B, with a much stronger peak $\Delta\lambda_{PHOSPHOR}$ between 500 nm and 750 nm, peaking at around 530 nm to 630 nm.

Figure 4:
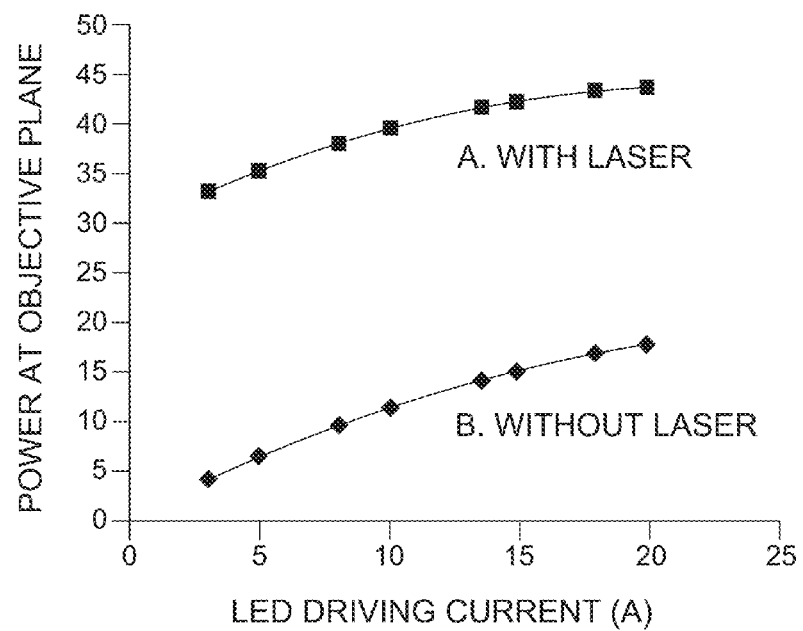
FIG. 4 shows experimental results comparing the optical output power of the light source module illustrated in FIG. 2, with and without laser pumping.

FIGS. 3 and 4 demonstrate that under normal operation of this phosphor based LED 110, even when driven at higher current or voltage (i.e. the maximum driving current is limited by a maximum driving current density), the phosphor layer 114 is not saturated by the blue light emission from LED 112. Thus, supplementary optical pumping of the phosphor 114 using the pump laser 120 significantly increases the optical output $\Delta\lambda_{PHOSPHOR}$ from the phosphor at longer wavelengths, as shown by comparing the emission spectra A and B, in FIG. 3. In particular, by selecting an appropriate phosphor LED 110, having a phosphor emission in the 500 nm to 700 nm range, and preferably having a peak in the range from 530 to 630 nm, high brightness illumination can be provided at these wavelengths, i.e. even within the green gap.

FIG. 4 shows the optical output of light source module 100-1 as a function of LED drive current with and without supplementary laser optical pumping of the phosphor layer. That is, FIG. 4 compares the optical power at the objective plane of a fluorescence imaging system, when operating the white light LED with and without laser pumping, using a 40× objective and an excitation filter to provide an illumination band from 545 nm to 575 nm. For operation at the maximum driving current, with laser pumping, the output of the light source unit 100 in this wavelength band was increased 2-3 times at the maximum driving current, compared to operation of the same white light phosphor LED 110 without supplementary laser pumping of the phosphor layer.

Thus, by way of example, the light source module 100-1 for illumination system 1000-1 comprises a first light source 110 comprising the LED1 112 emitting $\lambda_1$ in the range 445 nm to 475 nm having a phosphor 114 emitting $\Delta\lambda_{PHOSPHOR}$ in the range 500 nm to 750 nm, which is pumped by the second light source 120 comprising the laser emitting $\lambda_2$ at 440 nm. The band edge wavelength $\lambda_D$ of the dichroic element is selected at 443 nm, i.e. between $\lambda_1$ and $\lambda_2$, and arranged to reflect the laser wavelength $\lambda_2$, and transmit $\lambda_1$ and $\Delta\lambda_{PHOSPHOR}$. Thus, the optical output of the illumination module 100 comprises $\lambda_1 + \Delta\lambda_{PHOSPHOR}$.

Referring again to FIG. 2, optionally, if it is required to provide another light source 100-2, i.e. comprising an LED 130 (LED3) emitting another wavelength band $\lambda_3$, the dichroic beam-splitter/combiner 116 provides a compact and convenient way to couple light of wavelength $\lambda_3$ from LED 130 to the primary optical axis. As illustrated, the dichroic beam-splitter/combiner 116 has a pass band edge selected to reflect the laser emission at the laser wavelength $\lambda_2$, and transmit emission at $\lambda_1$ from the LED 110 and $\Delta\lambda_{PHOSPHOR}$ from the phosphor, and also reflect $\lambda_3$, the output emission comprises $\lambda_1$ and $\Delta\lambda_{PHOSPHOR}$ and $\lambda_3$. Thus, the combined optical output $\lambda_1 + \Delta\lambda_{PHOSPHOR}$, and optionally $\lambda_3$, of the illumination system can be coupled to the optical input of a fluorescence imaging and analysis system, such as a slide scanner or fluorescence microscope, with suitable coupling optics (not shown in FIG. 2, see FIGS. 11 to 14). As is conventional, filters within the fluorescence imaging system provide for selection of appropriate wavelengths for broadband or narrowband illumination, e.g. standard wavelength bands for fluorescence analysis, just as they would be if a conventional lamp illumination system was used. Beneficially, the solid state illumination system of the embodiment not only provides high radiance illumination at selected wavelengths, but also provides other advantages of solid state light sources over conventional lamps, i.e. electronic control of illumination parameters, such as, intensity and pulse duration.

Figure 5:
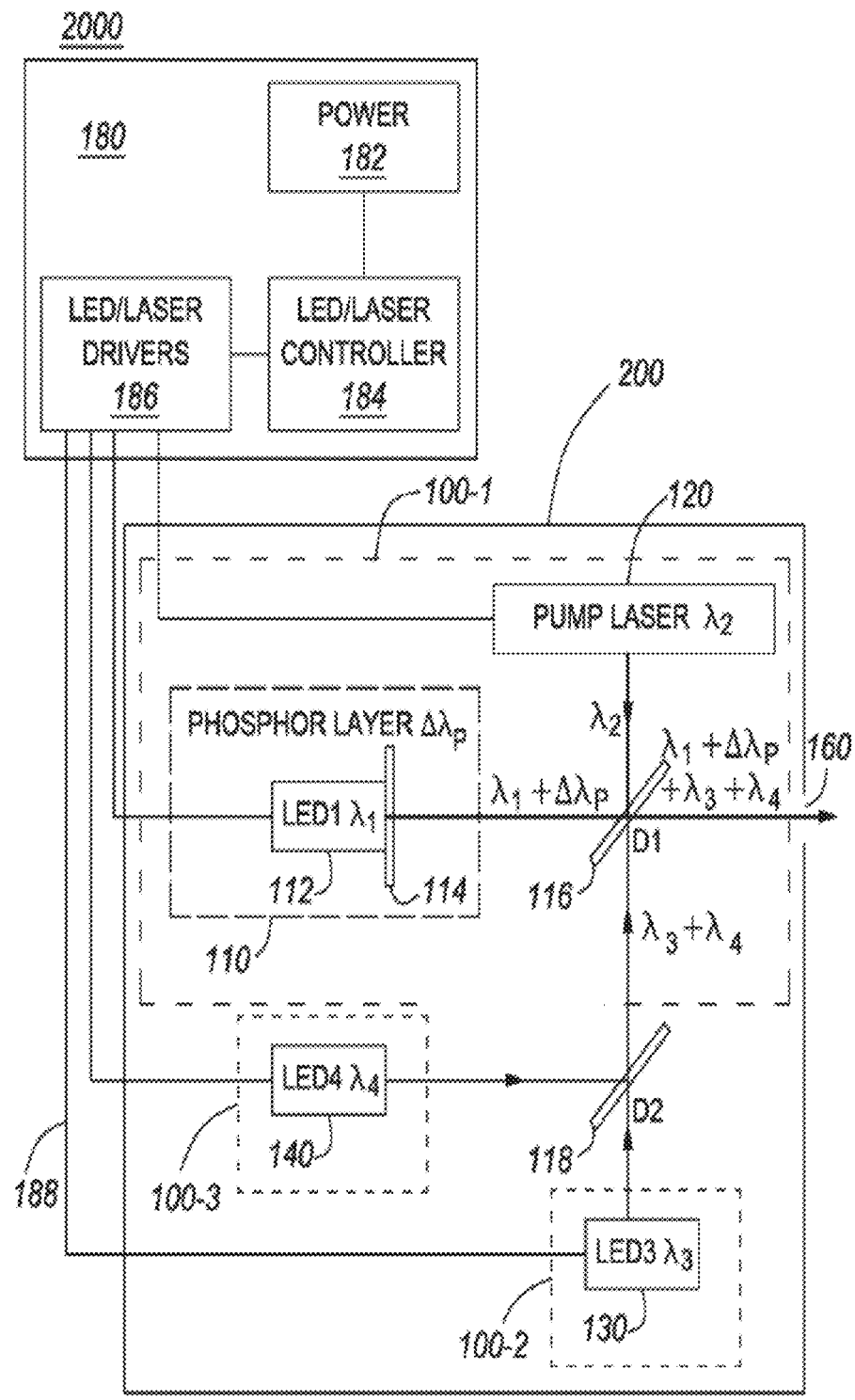
FIG. 5 illustrates schematically an illumination system according to a third embodiment, wherein a light source unit comprises a first light source module similar to that shown in FIG. 2, together with two additional LED light sources.

An illumination system 2000 according to a third embodiment is shown in FIG. 5. The light source unit 200 comprises a first light source module 100-1, comprising first and second light sources 110 and 120, identical to module 100-1 shown in FIG. 2. Like parts are labeled with the same reference numerals in each Figure. Additionally, a second light source module 100-2 comprises two additional light sources 100-2 and 100-3, i.e. a LED or LED arrays 130 and 140 for light emission at other wavelengths. A second dichroic element, i.e. beam-splitter/combiner 118 is provided, which has a band edge selected to combine the output of LED3 and LED4. That is, a LED 130 (LED3) provides light emission at $\lambda_3$, and a LED 140 (LED4) provides light emission at wavelength $\lambda_4$. For example, LED3 and LED4 may provide near ultraviolet (near UV) emission and UV emission respectively.

The drive system 180 is similar to that shown in FIG. 1, comprising a power supply 182, LED/laser controller 184 and LED/laser drivers 186 for driving each of the LED light sources, i.e. LEDs 110, 130 and 140 and laser 120. The additional dichroic element 118 is provided for coupling the output from the third and fourth light sources 130 and 140, and then combining other wavelengths, via the first dichroic element 116, along the primary optical axis, to couple each of the combined wavelengths, $\lambda_1$, $\Delta\lambda_P$, $\lambda_3$ and $\lambda_4$, to the output 160 of the light source unit 200.

For example, the first light source 110 may comprise a blue light emitting LED 112 emitting a wavelength $\lambda_1$ in the range from 445 nm to 475 nm, with a phosphor layer 114 emitting in $\Delta\lambda_{PHOSPHOR}$ in the 530 nm to 630 nm band. The second light source 120 comprises a laser emitting at $\lambda_2$, i.e. at 440 nm in the absorption band of the phosphor layer 114, and the dichroic element 116 has a 443 nm edge, i.e. as described with respect to the light source unit 100-1 shown in FIG. 2. To provide a combined UV/near UV illumination band, LED 130 comprises a near UV LED (LED3) providing near UV emission at $\lambda_3$, e.g. 410 nm to 445 nm, and LED 140 comprises a UV LED (LED4) providing UV emission at $\lambda_4$, e.g. 370 nm to 410 nm or 350 nm to 390 nm. In the configuration illustrated in FIG. 5, the second dichroic element 118 is provided which has a band edge to reflect the shorter wavelength UV emission at $\lambda_4$ from LED4 and transmit the longer wavelength emission $\lambda_3$ from LED3. The emission $\lambda_3 + \lambda_4$ is reflected by the first dichroic element 116 and redirected to the optical output 160. That is, LED3 and LED4 can cover wavelengths in the near UV and UV bands which are reflected by the first dichroic element 116, i.e. wavelengths shorter than the 443 nm band edge. Thus, the illumination system 2000 provides for high brightness illumination covering the UV, near UV, blue, green, yellow and red, to the near infrared regions. With suitable choices of $\lambda_1$, $\lambda_2$, $\Delta\lambda_{PHOSPHOR}$, $\lambda_3$, $\lambda_4$, the system can provide sufficient intensity at each wavelength commonly used for fluorescence imaging and analysis.

Figure 6:
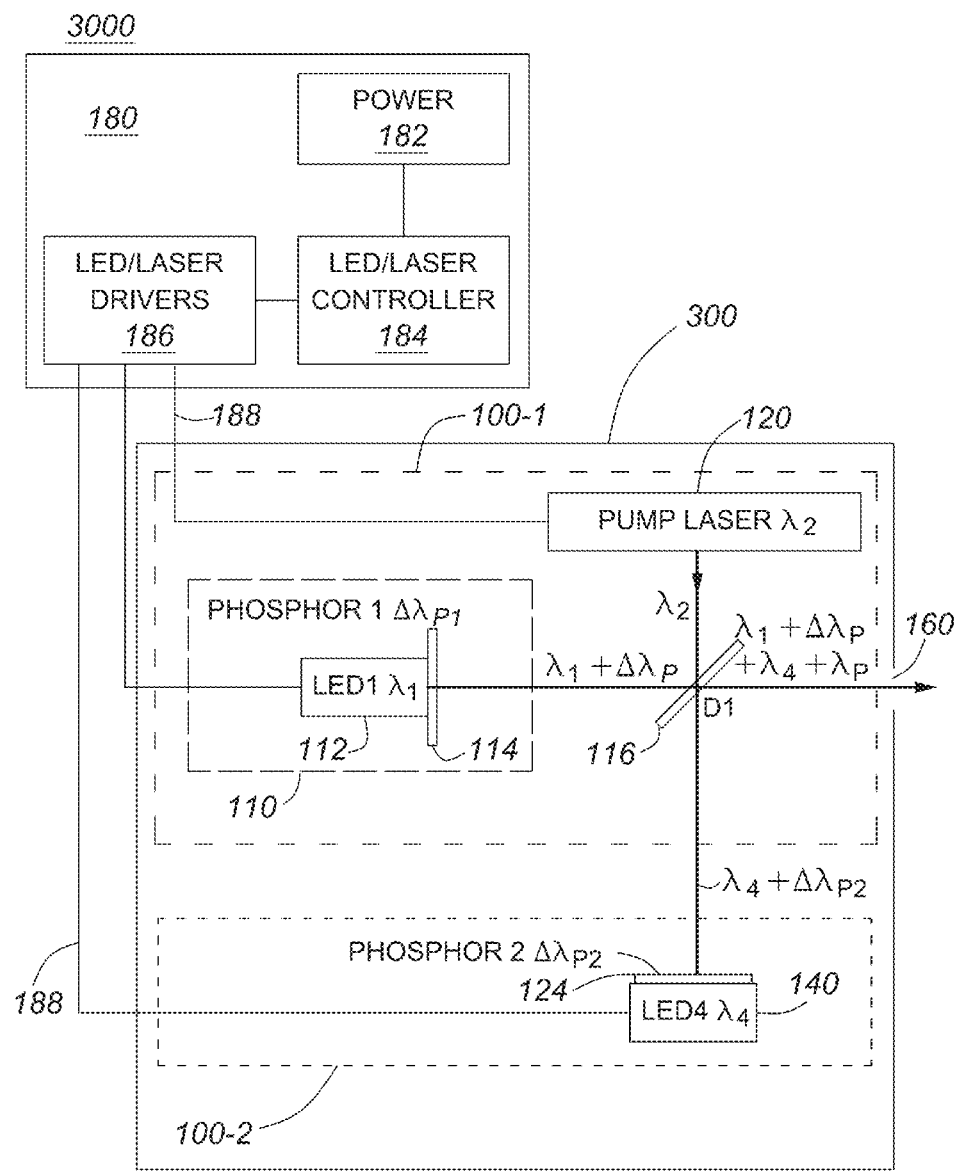
FIG. 6 illustrates schematically an illumination system according to a fourth embodiment, wherein a light source unit comprises a first light source module similar to that shown in FIG. 2, together with a second light source module.
Figure 7:
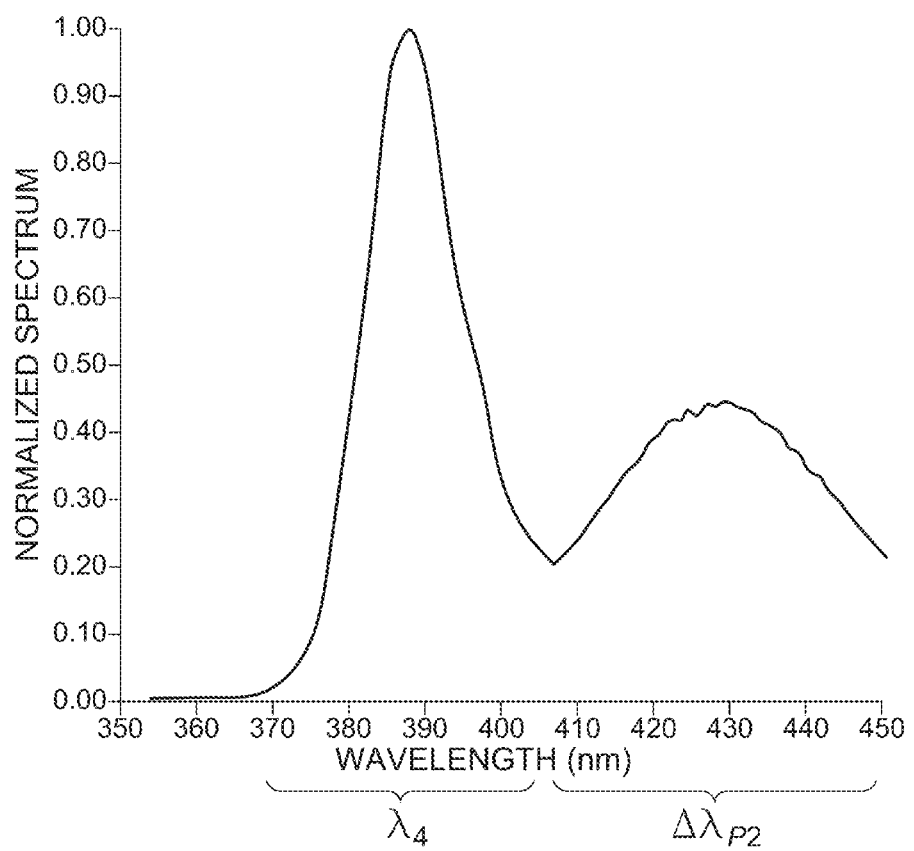
FIG. 7 shows an output spectrum of the second light source module shown in FIG. 6.

An illumination system 3000 according to a fourth embodiment is shown in FIG. 6. This system comprises a first light source module 100-1 identical to unit 100-1 shown in FIG. 2 and module 100-1 shown in FIG. 5. Thus, it comprises a first light source 110 comprising LED 112 (LED1) and its phosphor layer 114 (Phosphor1) and a second light source comprising the pump laser 120, providing output emission at $\lambda_1$ and $\lambda\lambda_{P1}$. The second light source 100-2 module comprises a LED 140 (LED4) and a different phosphor layer 124 (Phosphor2). For example, to provide a UV and near UV band, LED 4 comprises a UV LED, providing UV emission $\lambda_4$ at 370-410 nm or 350-390 nm, for exciting Phosphor2. Phosphor2 provides a near UV emission band, $\Delta\lambda_{P2}$, e.g. 410-445 nm. A sample emission spectrum of the second illumination module, comprising $\lambda_4$ and $\Delta\lambda_{P2}$, is shown in FIG. 7. As explained with reference to FIG. 5, since $\lambda_4$ and $\Delta\lambda_{P2}$ are shorter than the 443 nm band edge of the dichroic element 116, they will be reflected and redirected to the optical output 160 of the illumination unit.

Figure 8:
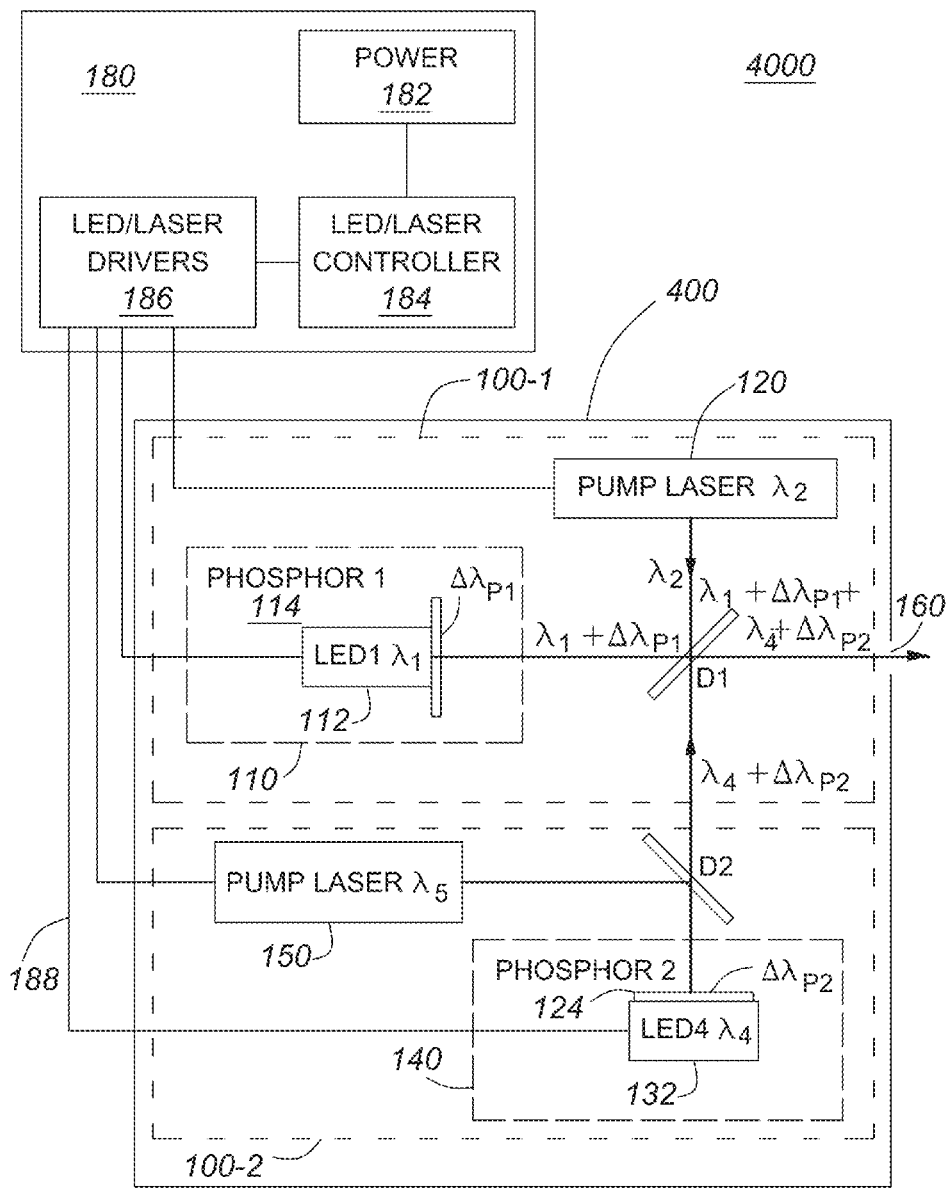
FIG. 8 illustrates schematically an illumination system according to a fifth embodiment wherein the light source unit comprises a first light source module and a second light source module.
Figure 9:
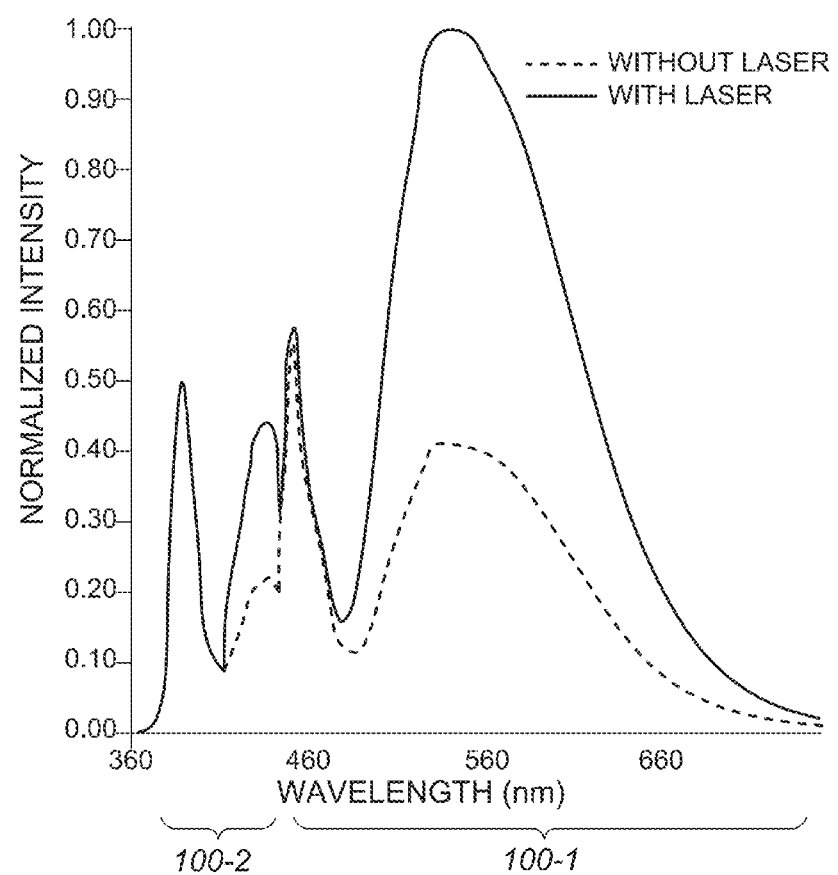
FIG. 9 shows the spectral output of the first and second light source modules of FIG. 8: A. without laser pumping of either module, and B. with laser pumping of both modules.

An illumination system 4000 according to a fifth embodiment is shown in FIG. 8. An illumination unit 400 comprises first and second illumination modules 100-1 and 100-2. The first illumination module 100-1 is identical to module 100-1 illustrated in FIGS. 2 and 5. The second illumination module 100-2 is a similar laser pumped phosphor LED, i.e. phosphor LED 130, comprising LED 140 (LED4) emitting $\lambda_4$, phosphor layer 124 (Phosphor2) emitting $\Delta\lambda_{P2}$, and a pump laser 150 emitting laser wavelength $\lambda_5$. In this embodiment, to provide a UV and near UV band and $\lambda_4$ and $\Delta\lambda_{P2}$, the light source module 100-2 comprises LED4 emitting in a UV band, e.g. 375-410 within an absorption band of Phosphor2, and Phosphor2 emitting in the near UV band, e.g. 410-445 nm. The dichroic element 118 is positioned to reflect the pump laser emission at $\lambda_5$ and transmit the LED4 emission at $\lambda_4$. That is, second dichroic element 118 has a passband edge between the LED5 laser wavelength $\lambda_5$ and the LED4 wavelength $\lambda_4$, e.g. 373 nm. The resulting output emission spectrum of system 4000 is shown in FIG. 9: spectrum A:

without laser pumping of light source module 100-1 or 100-2; and spectrum B: with laser pumping of both modules 100-1 and 100-2. These spectra demonstrate the significant increase in emission intensity of both Phosphor 1 and Phosphor2 emission, with laser pumping.

Figure 10:
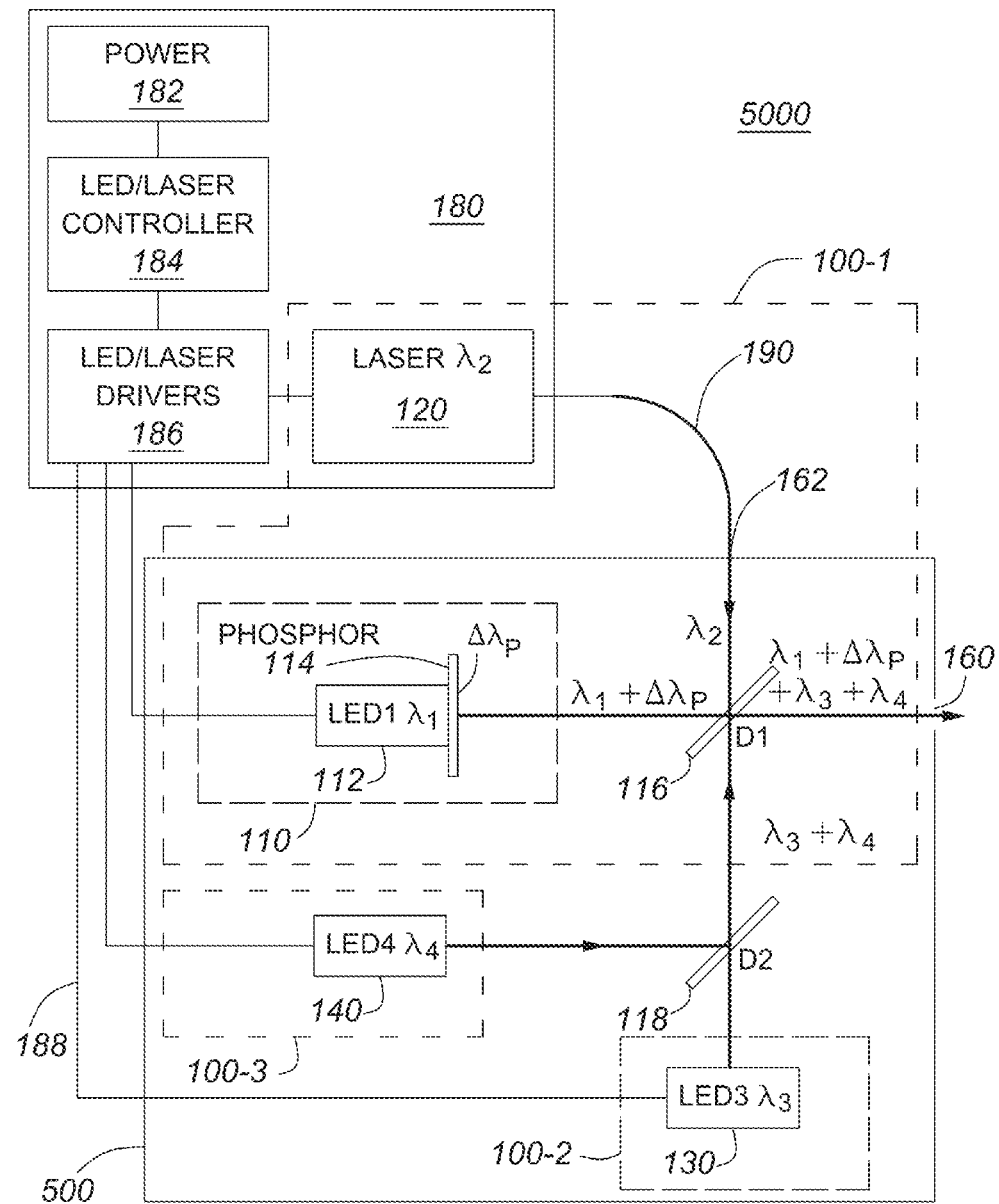
FIG. 10 illustrates schematically an illumination system according to a sixth embodiment, similar to that shown in FIG. 5, except that the pump laser is coupled by a flexible fiber light guide to the first light source unit.

An illumination system 5000 according to a fifth embodiment, comprising a light source unit 500 is illustrated in FIG. 10. This system is similar to that shown in FIG. 5, and all like components are labeled with the same reference numerals. This embodiment differs from that shown in FIG. 5 in that the pump laser 120 (Laser2) is housed within the control unit 180 instead of within the light source unit 500. The output of the pump laser is coupled by a flexible light guide 190 to an input 162 of the light source unit 500, and then directed by the dichroic element 116 for pumping of the phosphor layer 114.

In each of the embodiments described above, the pump laser system 120 may comprise a solid state laser, e.g. a single laser diode or a laser diode array. Each LED light source may comprise a single LED or a LED array. The phosphor layer for LED1 is integrated with LED1, i.e. a direct die contact layer or coating deposited on LED1, or a phosphor suspended in an encapsulant such as silicon, also in direct contact with LED 1. The Phosphor2 layer for LED4 is similarly integrated with LED4. In a variation of the module 100-2 shown in FIG. 6, Phosphor1 or Phosphor2 may be a remote phosphor layer, e.g. a phosphor coating on a separate substrate, pumped by (non-laser) LED1 or LED4. While specific arrangements of dichroic elements, i.e. beamsplitters and combiners, have been described it will be appreciated that other arrangements of these elements can be provided. In particular the wavelengths of each light source element may be combined or split by suitable choices of the bandpass or band edge of each dichroic element.

To simplify optical coupling, it is preferable that each dichroic element is selected to reflect the pump laser wavelengths, i.e. $\lambda_2$ or $\lambda_5$, in the embodiments described above. Additionally, to provide for effective optical coupling of the pump laser to the phosphor layer and efficient collection of the light emission from each light source, optical coupling elements such as lenses or optical concentrators are used. For simplicity these elements are not shown in the preceding Figures. FIGS. 11 to 14 show further details for arrangements of these optical coupling elements, by way of example.

Figure 11:
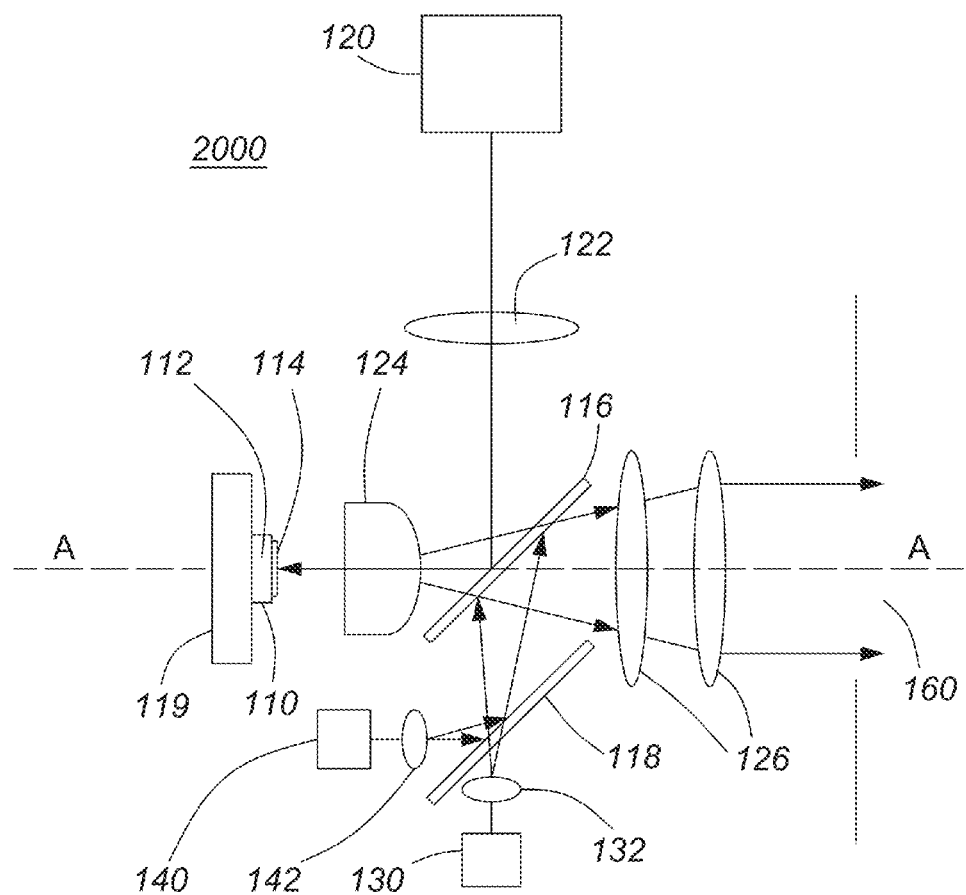
FIG. 11 shows a first arrangement of optical elements for coupling emission of one or more wavelengths, from a light source unit as illustrated in FIG. 5, along a primary optical axis to the optical output of the illumination system.

FIG. 11 shows an arrangement of optical coupling elements for the system illustrated in FIG. 5. Like parts are labeled with the same reference numerals. For thermal management, the phosphor LED 110 comprising LED 112 (LED1) and phosphor layer 114 is mounted on a copper plate 119 which is cooled by water or forced air. Focusing and collection optics comprise lens 122, which collects light emission from the pump laser 120. The pump laser light $\lambda_2$ is reflected from dichroic element 116, and collected by collection lens 124 to focus the pump laser light $\lambda_2$ onto the phosphor layer 114. Light emission at $\lambda_1$ and $\Delta_{PHOSPHOR}$ is collected by collection lens 124, transmitted by the dichroic element 116 and collimated by output coupling lenses 126 for coupling to the optical output 160 of the illumination system, e.g. to an optical input of a fluorescence imaging and analysis system or to an optical input of a microscope (not shown). Emission from the LEDs 130 and 140 is collected by lenses 132 and 142, respectively, and coupled through the second dichroic plate 118, the first dichroic plate 116 and the output coupling lenses 126 to the optical output 160.

Figure 12:
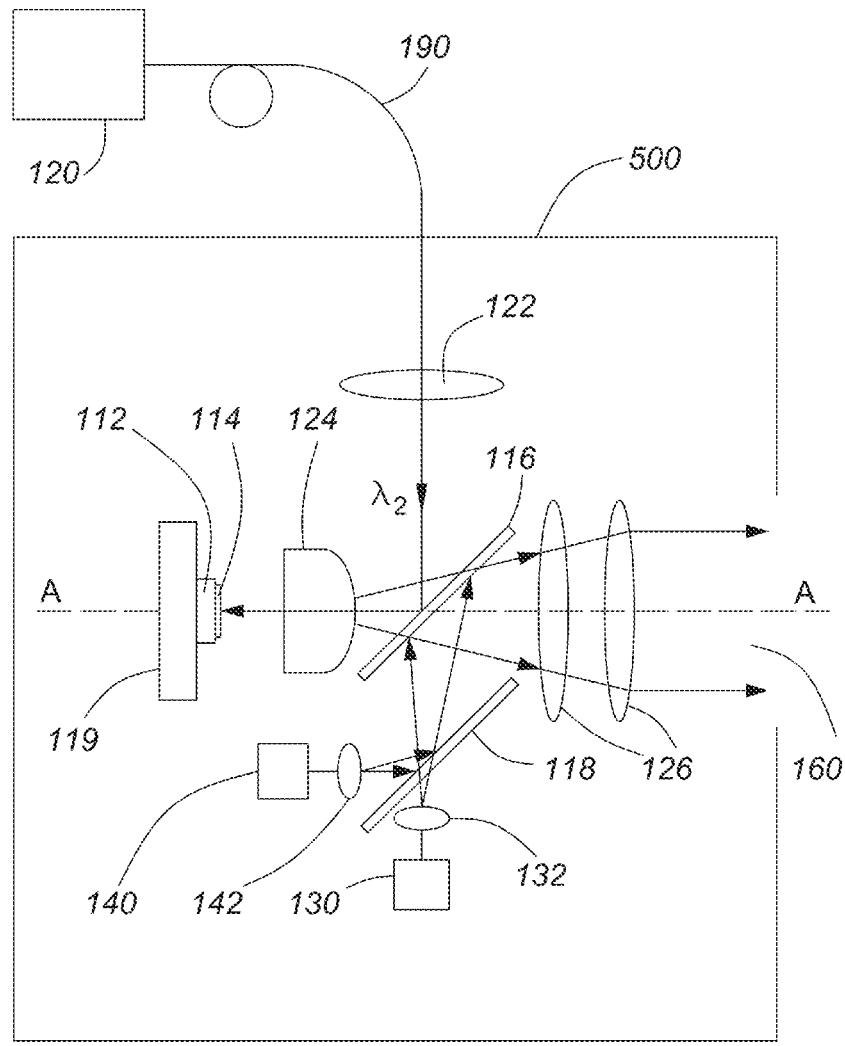
FIG. 12 shows a second arrangement of optical elements for coupling emission of one or more wavelengths, from a light source unit as illustrated in FIG. 10, along a primary optical axis to the optical output of the illumination system.

FIG. 12 shows an arrangement of optical coupling elements for a system such as illustrated in FIG. 10. This arrangement is similar to that shown in FIG. 8, except that the pump laser 120 is housed externally of the light source unit, for example within the control unit 180 as shown in FIG. 8, and the pump laser radiation is coupled to an input 162 of the light source unit 500 via a flexible optical light guide 190.

Figure 13A:
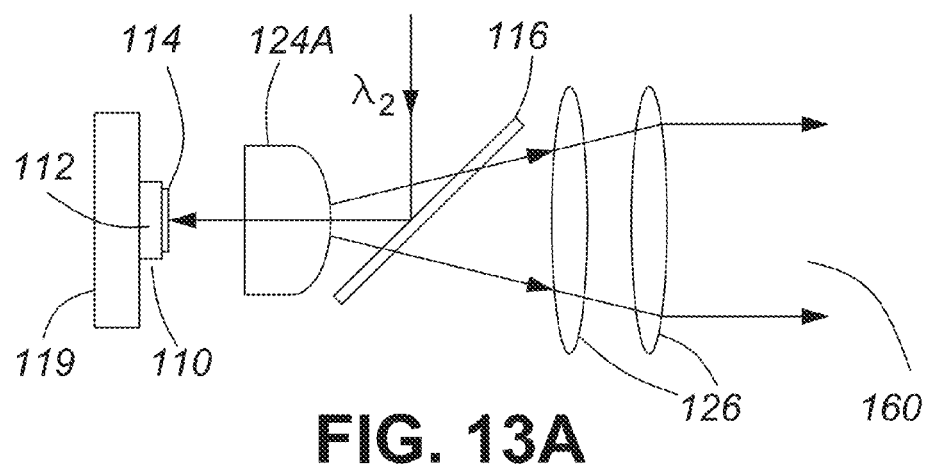
FIGS. 13A-C show three configurations of optical elements for coupling of the pump laser to the phosphor layer of the LED1 using respectively: 13A. a lens; 13B. a Compound Parabolic Concentrator (CPC); and 13C. a taper.
Figure 13B:
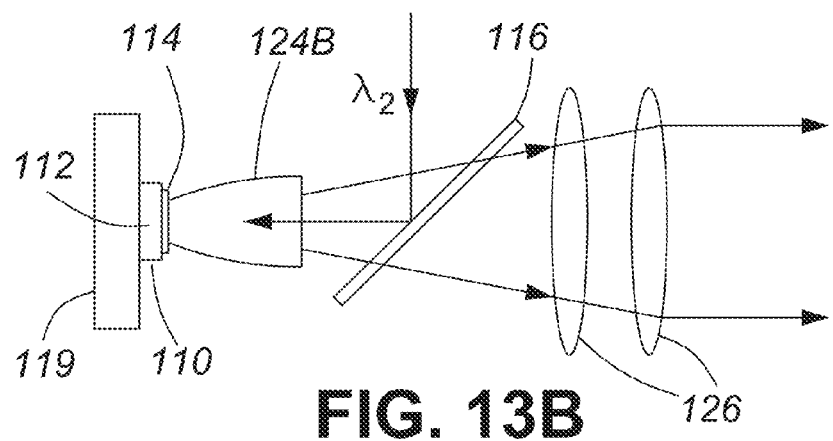
Figure 13C:
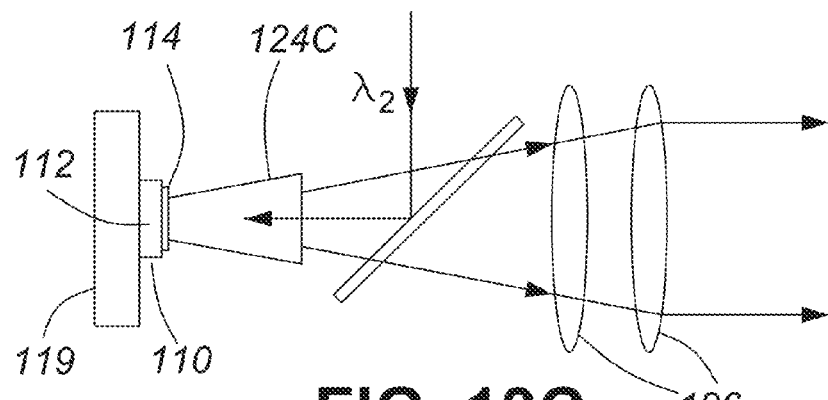

FIGS. 13A, B and C show three variants of the arrangement of optical coupling elements shown in FIG. 10. In FIG. 13B the coupling lens 124A of FIG. 13A is replaced by a compound parabolic concentrator 124B, and in FIG. 13C a conical tapered concentrator 124C is used. Other optical coupling elements are similar to those shown in FIG. 11.

Figure 14:
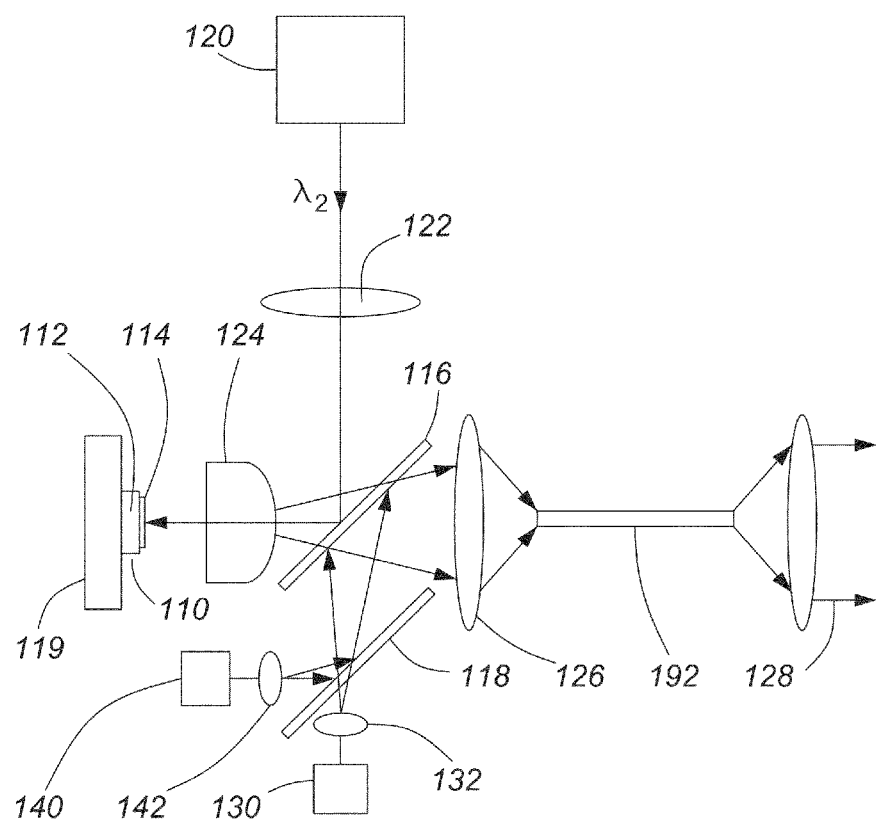
FIG. 14 shows an arrangement of optical elements for coupling emission of one or more wavelengths, from a light source unit as illustrated in FIG. 4, to an optical input of a fluorescence microscope system, using a liquid light guide.

In another variant of the optical coupling elements, shown in FIG. 14, the optical emission transmitted or reflected towards the optical output is collected by output coupling lens 126 and focused onto the input of an optical light guide 192, which may be a liquid light guide, for coupling to an input coupling lens 128 of a fluorescence imaging system, such as a fluorescence microscope or slide scanner. Again, other optical coupling elements are similar to those shown in FIG. 11 and are labeled with like reference numerals.

In summary, a solid state high radiance illumination source as disclosed herein is capable of providing for high intensity illumination at each of a number of wavelengths commonly used for fluorescence analysis and imaging. The laser pumped LED and arrangement of optical components provide for a compact light source unit that may comprise one or more individual LED light sources or LED light source modules, providing different wavelength outputs. The system provides an alternative to conventional arc lamps, and addresses limitations of other available solid state LED light sources to provide high brightness at selected wavelengths, particularly in the 530 nm to 630 nm range.

The high radiance solid state illumination system also provides advantages over conventional lamp illumination sources, for example, allowing for electronic control of intensity and pulse generation as disclosed in copending PCT International patent application no. PCT/CA2012/00446 entitled "Light Source, Pulse Controller and Method for Programmable Pulse Generation and Synchronization of Light Emitting Devices".

Figure 15:
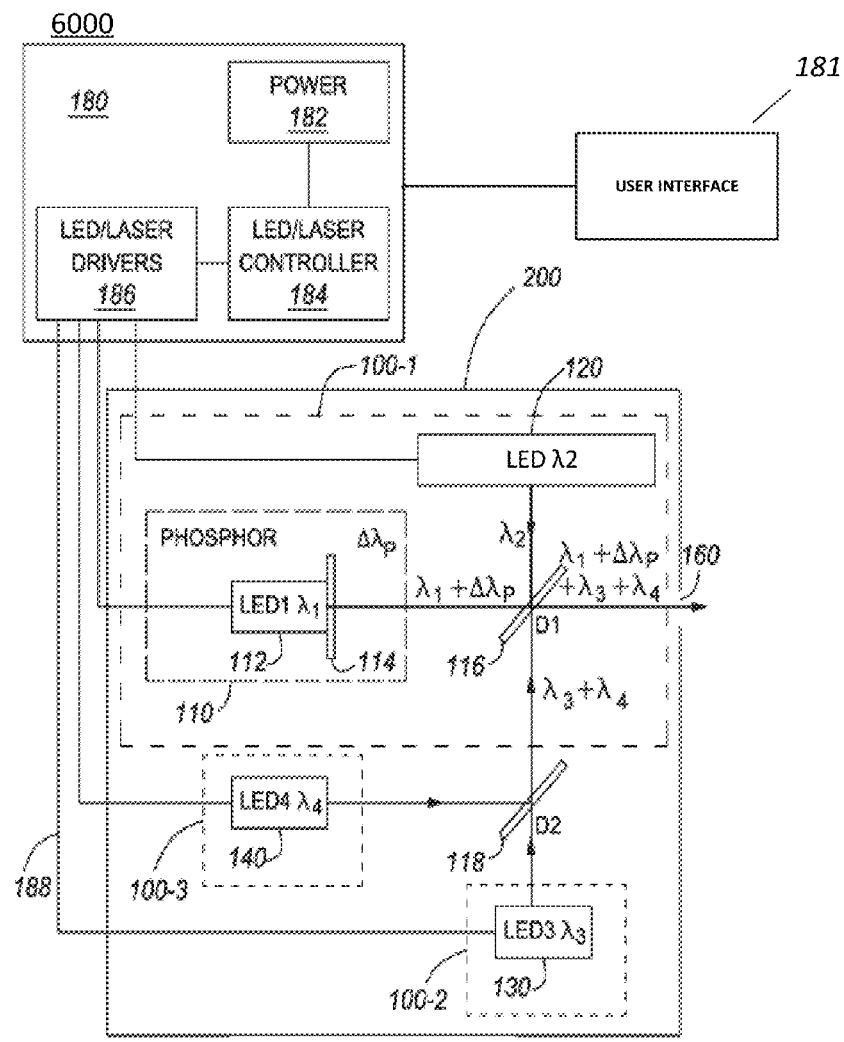
FIG. 15 illustrates schematically an illumination system according to another embodiment.

FIG. 15 is a schematic representation of an exemplary illumination system 6000 (e.g., for fluorescence imaging and/or analysis). The system 6000 is similar in some ways to the system 2000 in FIG. 5.

The illustrated system 6000 has a control unit 180, a light source unit 200, and a user interface 181.

The light source unit 200 includes a first light source module 100-1 (with a first light source 112, a phosphor light source 114, a second light source 120, and a first dichroic optical element (D1) 116), a second light source module 100-2 (with a third light source 130), a third light source module 100-3 (with a fourth light source 140) and a second dichroic element (D2) 118. Each of the first, second, third, and fourth light sources 112, 120, 130 and 140 in the illustrated implementation is a light emitting diode (LED). Of course, in various implementations, any or all of these may be a different kind of light source. In some implementations, any or all of these may be a laser. In one exemplary alternative configuration, the second light source 120 is a laser, while the first light source 112, the third light source 130, and the fourth light source 140 are light emitting diodes.

The control unit 180 has a power supply 182, a controller 184 and drivers 186, which are coupled by electrical connections 188 to the light source unit 200. The control unit 180 is generally adapted to control the light source unit 200.

In various implementations, including the one shown in FIG. 15, the phosphor light source 114 is a physically attached to the first light source 112 (e.g., as a layer of phosphor applied to a surface of the first light source 112). In other implementations, the phosphor light source 114 is physically separate from the first light source 112. If physically separate, the phosphor light source 114 may take the form of a ceramic or single crystal phosphor substrate, for example.

The first light source 112 is configured to emit light at a first wavelength $\lambda_1$ within an absorption band of the phosphor light source 114. The second light source is configured to emit light at a second wavelength $\lambda_2$ also within the absorption band of the phosphor light source 114. The third light source 130 is configured to emit light at a third wavelength $\lambda_3$. The fourth light source 140 is configured to emit light at a fourth wavelength $\lambda_4$. The phosphor light source 114 is configured (e.g., when being pumped or excited) to emit light having a wavelength in a wavelength band $\Delta\lambda_{PHOSPHOR}$. In a typical implementation, the wavelength of light emitted by the phosphor light source 114 is longer than the first wavelength $\lambda_1$.

The controller 180 is configured to drive the first, second, third and/or fourth light sources, concurrently or otherwise. For example, in some implementations, the controller 180 is adapted to drive the first light source 112 and the second light source 120 to pump the phosphor light source 114 concurrently. In some implementations, the controller 180 is adapted to drive only one of the first light source 112 or the second light source 120 at a given time to pump the phosphor light source, without concurrently driving the other. For example, in one implementation, the controller 180 is adapted to drive the second light source 120 to optically pump the phosphor light source 114 without concurrently driving the first light source 112 to optically pump the phosphor light source 114. In a typical implementation, one or more (or both) of the third light source 130 and fourth light source 140 are configured to operate while the phosphor light source 114 is being pumped.

The first dichroic optical element (D1) 116 in the illustrated implementation is configured to: 1) direct light emitted by the second light source 120 at the second wavelength $\lambda_2$ onto the phosphor light source 114, 2) direct light emitted by the phosphor light source 114 in the wavelength band $\Delta\lambda_{PHOSPHOR}$ (and, optionally, light emitted by the first light source 112 at the first wavelength $\lambda_1$) to an optical output 160 of the illumination system, 3) direct light emitted by the third light source 130 at the third wavelength $\lambda_3$ to the optical output 160 of the illumination system, and 4) direct light emitted by the fourth light source 140 at the fourth wavelength $\lambda_4$ to the optical output 160 of the illumination system.

The second dichroic optical element (D2) 118 in the illustrated implementation is configured to: 1) direct the light emitted by the third light source 130 at the third wavelength $\lambda_3$ to the first dichroic optical element (D1) 116, and 2) direct the light emitted by the fourth light source 140 at the fourth wavelength $\lambda_4$ to the first dichroic optical element (D1) 116.

Light emitted from each respective one of the first, second, third and fourth light sources 112, 120, 130, 140 follows a particular path through the illustrated light source unit 200. In this regard, light from the first light source 112 (if energized) is directed onto the phosphor light source 114 and travels through the first dichroic optical element (D1) 116 to the optical output 160. Light from the second light source 120 is directed by the first dichroic light source (D1) 116 onto the phosphor light source 114. Light from the phosphor light source 114 travels through the first dichroic optical element (D1) 116 to the optical output 160. Light from the third light source 130 travels through the second dichroic optical element (D2) 118 and is then reflected by the first dichroic optical element (D1) 116 to the optical output 160. Light from the fourth light source 140 is reflected by the second dichroic optical element (D2) 118 toward the first dichroic optical element (D1) 116 and is then reflected by the first dichroic optical element (D1) 116 toward the optical output 160.

Thus, in the illustrated implementation, light from the third light source 130 and light from the fourth light source 140 travel between the first dichroic optical element (D1) 116 and the second dichroic optical element (D2) 118 along a first common optical path. Moreover, light emitted by the first light source 112 (if the first light source 112 is energized), light emitted by the phosphor light source 114, light emitted by the second light source 120, light emitted by the third light source 130, and light emitted by the fourth light source 140 travel from the first dichroic optical element (D1) 116 to the optical output 160 along a second common optical path.

In some implementations, the illustrated system is operable within and switchable between multiple operating modes. These operating modes can include, for example, any two or more of the following: a first operating mode (e.g., a low power mode) in which only the first light source 112 is optically pumping the phosphor light source 114, a second operating mode (e.g., a medium power mode) in which only the second light source 120 is optically pumping the phosphor light source 114, and a third operating mode (e.g., a high power mode) in which the first light source 112 and the second light source 120 are concurrently optically pumping the phosphor light source 114. In some implementations, the illumination system is switchable between any or all three of these (and possibly more) operating modes.

If the system is operable within and switchable between multiple operating modes, in general, the controller 180 typically implements any switching that happens. Moreover, in some implementations, the system has a user interface device 181 (e.g., a knob, toggle switch, touch screen, etc.) that enables a user to specify which of the available operating modes (e.g., low power/intensity, medium power/intensity or high power/intensity) the system should be operating in. In these implementations, the controller 180 can be configured to implement the switching in response to an instruction from the user interface device 181. In some implementations, the system can be adapted to switch between available operating modes automatically (i.e., without specific input from a human at the time of the switching). In these implementations, the switching may occur automatically in response to a software instruction, a timing signal, or the like.

Figure 16:
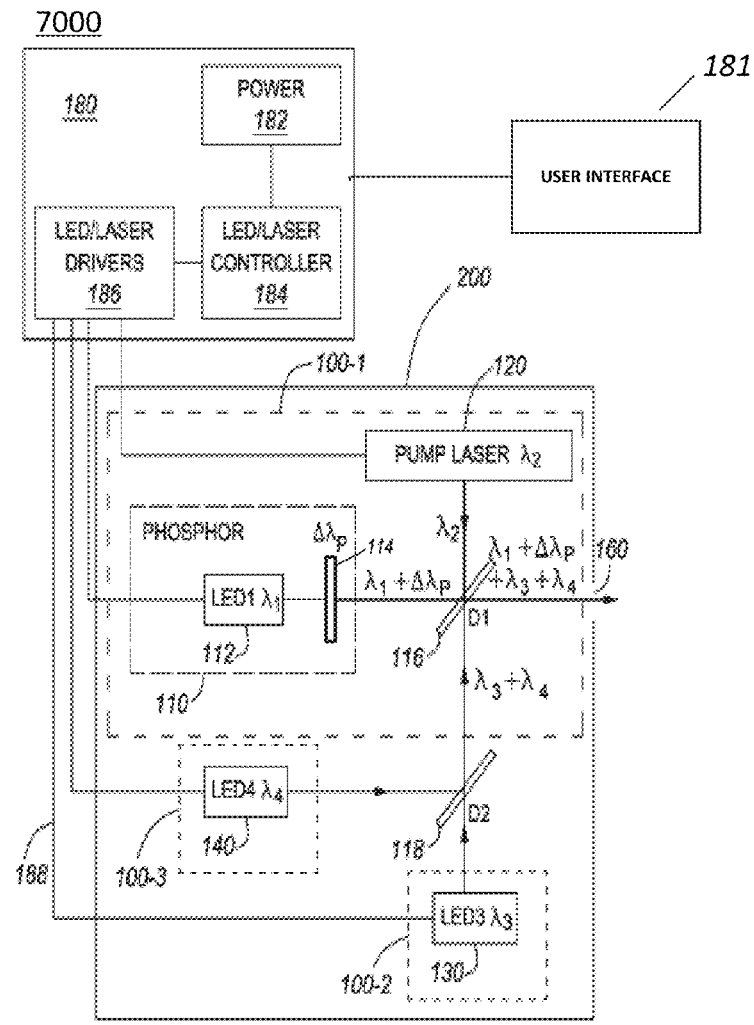
FIG. 16 illustrates schematically an illumination system according to yet another embodiment.

FIG. 16 shows another exemplary illumination system 7000 that is in some ways similar to system 6000 in FIG. 15. In system 7000 the second light source 120 is a pump laser (though it could, of course, alternatively, be an LED), and in system 7000 the phosphor light source 114 is physically separate from the first light source 112.

Figure 17:
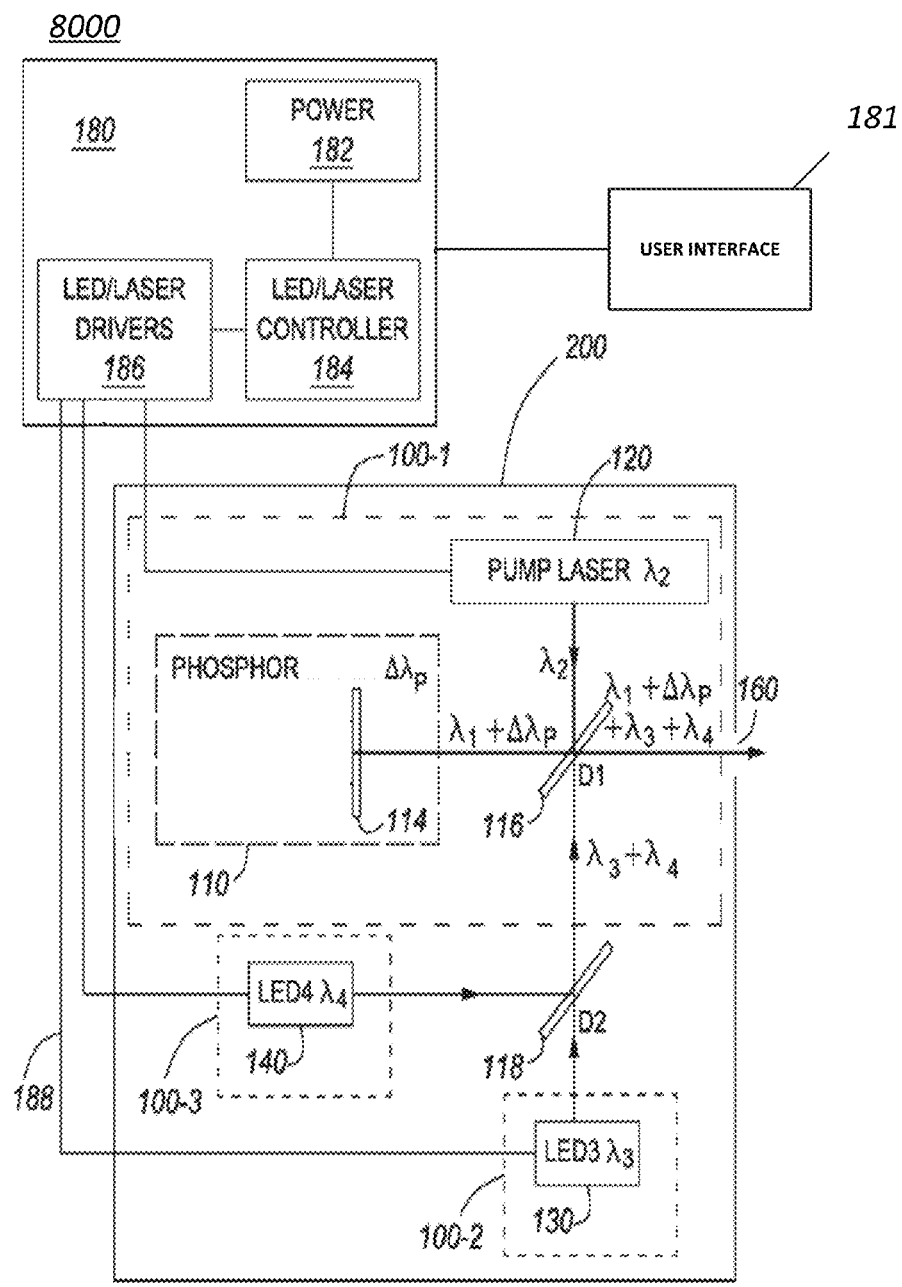
FIG. 17 illustrates schematically an illumination system according to even another embodiment.

FIG. 17 shows an exemplary illumination system 8000 that is similar in some ways to system 7000 in FIG. 16. In system 8000 there is no first light source (e.g., 120 in FIG. 16)—and the phosphor light source 114 is a physically stand-alone component. In the illustrated system 8000, only the second light source 120 is configured to pump the phosphor light source 114.

Figure 18:
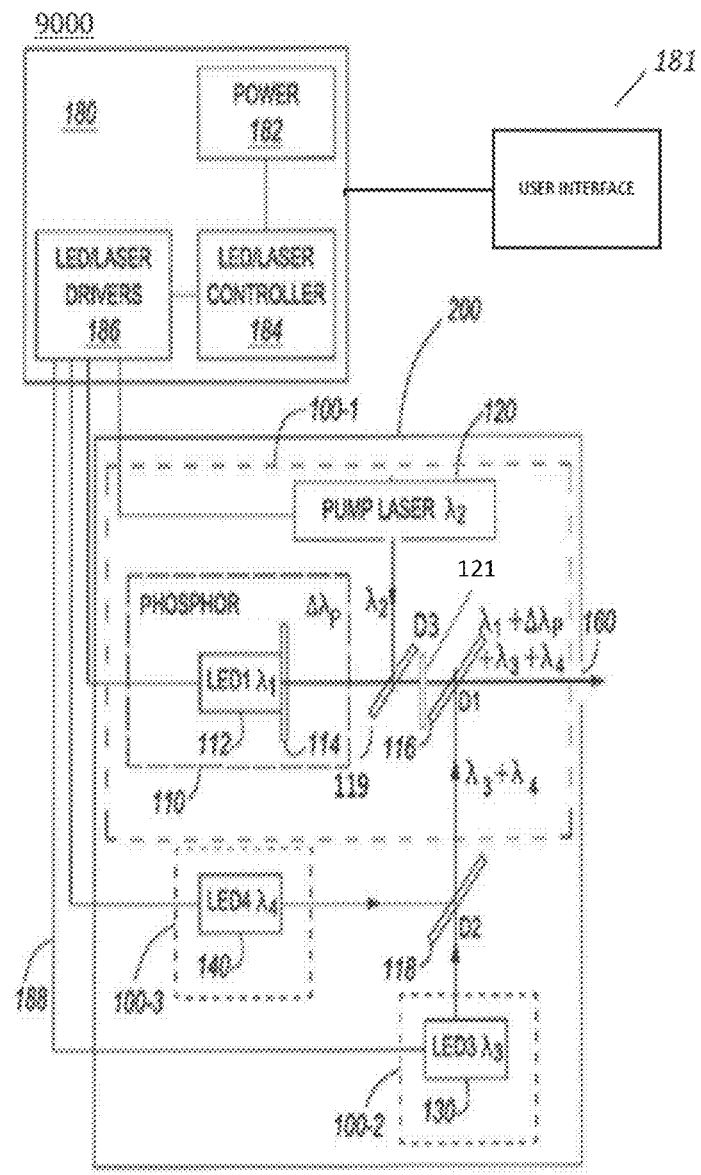
FIG. 18 illustrates schematically an illumination system according to still another embodiment.
Figure 19:
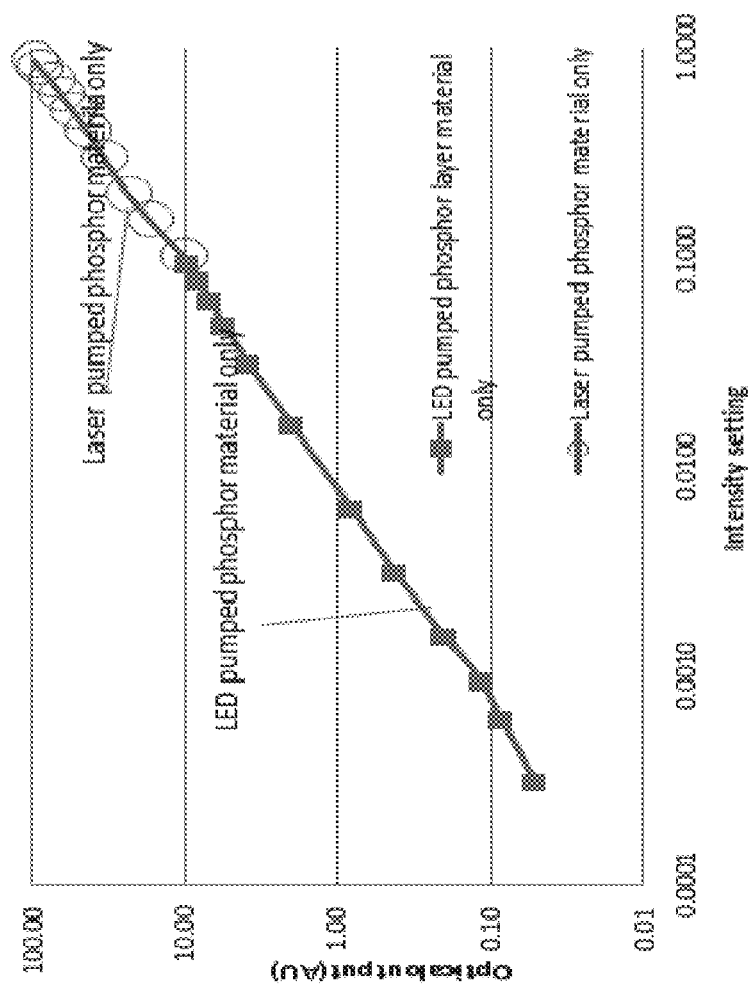
FIG. 19 is a chart showing a prophetic example of optical output vs. intensity setting in an exemplary illumination system with more than one operating mode.

FIG. 18 shows an exemplary illumination system 9000 that is similar in some ways to system 6000 in FIG. 15. In system 9000, however, 1) the second light source 120 is a pump laser, 2) there are three (instead of two) dichroic optical elements: a first dichroic optical element (D1) 116, a second dichroic optical element (D2) 118 and a third dichroic optical element (D3) 119, and 3) there is an optical filter 121 between the third 119 and first 116 dichroic optical elements. In a typical implementation, the optical filter 121 is configured to filter out a portion of light emitted by the phosphor light source 114—so that only a portion of the phosphor emission spectrum is combined with the other wavelengths.

Due to the extra optical elements and the different overall configuration in system 9000 as compared to the system 6000 in FIG. 15, some of the optical light paths that the light from the different light sources follow are somewhat different as well.

For example, in system 9000, light from the first light source 112 is directed onto and pumps the phosphor 114, travels through the third dichroic optical element 119, may be (or may not be) partially filtered by the optical filter 121 travels through the first dichroic optical element 116 and through the optical output 160. Light from the second light source 120 is reflected by the third dichroic optical element 119 onto the phosphor 114 to pump the phosphor 114. Light from the third light source 130 travels through the second dichroic optical element 118, is reflected by the first dichroic optical element and travels through the optical output 160. Light from the fourth light source 140 is reflected by the second dichroic optical element 118 and reflected again by the first dichroic optical element 116 and then travels through the optical output 160.

In various implementations, one or more of the systems disclosed herein may be operable within and switchable between multiple operating modes. These operating modes can include, for example, any two or more of the following: a first operating mode (e.g., a low power mode) in which only a first light source 112 is optically pumping the phosphor light source 114, a second operating mode (e.g., a medium power mode) in which only a second light source 120 is optically pumping the phosphor light source 114, and a third operating mode (e.g., a high power mode) in which the first light source 112 and the second light source 120 are concurrently optically pumping the phosphor light source 114. An illumination system may be switchable between any or all three of these (and possibly more) operating modes.

If a system is operable within and switchable between multiple operating modes, in general, the controller 180 typically implements any switching that happens. Moreover, in some implementations, if the system has a user interface device (i.e., device 181 in FIGS. 15-18), the user interface device enables a user to specify which of the available operating modes (e.g., low power/intensity, medium power/intensity or high power/intensity) the system should be operating in. In these implementations, the controller 180 can be configured to implement switching in accordance with or in response to any instructions it receives from the user via the user interface device (e.g., 181). In some implementations, the system can be adapted to switch between available operating modes automatically (i.e., without specific input from a human at the time of the switching).

In these implementations, the switching may occur automatically in response to a software instruction, a timing signal, or the like.

FIG. 16 is a chart showing a prophetic example of optical output vs. intensity setting (both represented by arbitrary units) in an exemplary illumination system (whose first light source 112 is an LED and whose second light source 120 is a laser, such as shown in FIG. 8) with more than one operating mode.

The chart in FIG. 16 includes information that relates to two operating modes: a first (lower optical output) operating mode, where only the LED 112 is pumping the phosphor material 114, and a second (higher optical output) operating mode, where only laser is pumping the phosphor material 114. In some implementations, the system might also have a third (even higher optical output) operating mode, where both the LED 112 and the laser are pumping the phosphor material 114 concurrently (e.g., on opposite sides of the phosphor material 114).

As shown in the chart of FIG. 16, the transition between one operating mode (e.g., the first (lower optical output) operating mode) and another operating more (e.g., the second (higher optical output) operating mode) is substantially linear. In general, this linearity can be achieved by properly calibrating the system (e.g., by ensuring that the user settings correlate with drive currents for the LED and the laser such that the optical output, particularly when transitioning between two different operating modes, is substantially linear).

In some implementations, the techniques and systems disclosed herein facilitate generating a relatively large amount of Yellow/Green light without increasing the size of the light emitting area and mixing this with other discrete LED wavelengths to form a broad spectrum light source. In a typical implementation, Yellow light is generated in the phosphor layer (or component) after absorbing blue light, which may be injected from the front of the layer (or component), from the back of the layer (or component), or from both. Also, in some implementations, pump 1 is LED1 and produces a Blue light, the Phosphor Layer is (but need not be) part of LED1, and pump 2 is a laser that produces Blue light. It has been found that, in practice, in some implementations, concurrently pumping the phosphor layer (e.g., with LED1 & a pump laser) may create a high heat load (e.g., on LED1—where the phosphor layer is integrated with LED1) and for many applications the pump laser and phosphor layer provided enough optical power, even when LED1 is not operational.

Although embodiments have been described in detail above by way of example, it will be apparent that modifications to the embodiments may be made. For example, each LED light source referred to as a LED, and it is apparent that each may be a single LED or an LED array of multiple LED, and the phosphor layer may be directly coated on the emitter surface of the LED or LED array, or provided as an overlying phosphor containing layer. For simplicity single optical elements such as lenses are illustrated, but compound lens or other suitable coupling optics may be used. It will also be apparent that additional LED light sources may be added and similarly optically coupled to the optical output using optical coupling elements comprising dichroic beamsplitter/combiners. However, to reduce reflective and transmissive losses, and reduce size and cost, it may desirable to provide a simple design with fewer components.

Additionally, various features from different implementations described herein may be combined in ways not explicitly shown in the drawings or otherwise described explicitly.

Although embodiments of the invention have been described and illustrated in detail, it is to be clearly understood that the same is by way of illustration and example only and not to be taken by way of limitation, the scope of the present invention being limited only by the appended claims.

What is claimed is:

1. An illumination system comprising:
 a phosphor light source configured to emit light having a wavelength in a wavelength band $\Delta\lambda_{PHOSPHOR}$;
 a second light source configured to emit light at a second wavelength $\lambda_2$ within an absorption band of the phosphor light source;
 a third light source configured to emit light at a third wavelength $\lambda_3$;
 a fourth light source configured to emit light at a fourth wavelength $\lambda_4$;
 a controller configured to drive the second light source, the third light source and the fourth light source;
 a first dichroic optical element configured to: 1) direct light emitted by the phosphor light source in the wavelength band $\Delta\lambda_{PHOSPHOR}$ to an optical output of the illumination system, 2) direct light emitted by the third light source at the third wavelength $\lambda_3$ to the optical output of the illumination system, and 3) direct light emitted by the fourth light source at the fourth wavelength $\lambda_4$ to the optical output of the illumination system; and
 a second dichroic optical element configured to: 1) direct the light emitted by the third light source at the third wavelength $\lambda_3$ to the first dichroic optical element, and 2) direct the light emitted by the fourth light source at the fourth wavelength $\lambda_4$ to the first dichroic optical element.

2. The illumination system of claim 1, wherein the first dichroic optical element is further configured to direct light emitted by the second light source at the second wavelength $\lambda_2$ onto the phosphor light source.

3. The illumination system of claim 1, further comprising a first light source configured to emit light at a first wavelength $\lambda_1$ onto the phosphor light source.

4. The illumination system of claim 3, wherein the phosphor light source is physically attached to the first light source.

5. The illumination system of claim 3, wherein the phosphor light source is physically separate from the first light source.

6. The illumination system of claim 5, wherein the phosphor light source is a ceramic phosphor or a single crystal phosphor.

7. The illumination system of claim 3, wherein the wavelength of the light emitted by the phosphor light source is longer than the first wavelength $\lambda_1$.

8. The illumination system of claim 3, wherein the controller is further configured to drive the first light source.

9. The illumination system of claim 3, wherein the first dichroic optical element is further configured to direct light emitted by the first light source at the first wavelength $\lambda_1$ along with the light emitted by the phosphor light source in the wavelength band $\Delta\lambda_{PHOSPHOR}$ to the optical output of the illumination system.

10. The illumination system of claim 3, wherein the first, third and fourth light sources are light emitting diodes.

11. The illumination system of claim 3, wherein the controller is configured to drive the second light source to optically pump the phosphor light source without concurrently driving the first light source to optically pump the phosphor.

12. The illumination system of claim 3, wherein the light emitted by the first light source at the first wavelength, the light emitted by the phosphor light source in the wavelength band $\Delta\lambda_{PHOSPHOR}$, the light emitted by the second light source at the second wavelength, the light emitted by the third light source at the third wavelength, and the light emitted by the fourth light source at the fourth wavelength travel from the first dichroic optical element to the optical output along a common optical path.

13. The illumination system of claim 3, wherein the illumination system is switchable between two or more of the following operating modes:
 a first operating mode in which only the first light source is energized to optically pump the phosphor light source;
 a second operating mode in which only the second light source is energized to optically pump the phosphor light source; and
 a third operating mode in which the first light source and the second light source are energized to optically pump the phosphor light source.

14. The illumination system of claim 13, wherein the illumination system is switchable between all three of the operating modes.

15. The illumination system of claim 13, wherein the controller is configured to implement any of the switching between the operating modes.

16. The illumination system of claim 15, further comprising a user interface device, wherein the controller is configured to implement the switching in response to an instruction from the user interface device.

17. The illumination system of claim 3, wherein the phosphor light source is configured to emit light in the wavelength band $\Delta\lambda_{PHOSPHOR}$ only in response to first absorbing light from the first or second light sources.

18. The illumination system of claim 1, wherein the second light source is a laser.

19. The illumination system of claim 1, wherein the second light source is a light emitting diode.

20. The illumination system of claim 1, wherein the light emitted by the third light source at the third wavelength $\lambda_3$ and the light emitted by the fourth light source at the fourth wavelength $\lambda_4$ travel between the first dichroic optical element and the second dichroic optical element along a common optical path.

21. The illumination system of claim 1, wherein the first light source, the third light source and the fourth light source are light emitting diodes.

22. The illumination system of claim 1, further comprising:
 a third dichroic optical element configured to 1) direct light emitted by the second light source at the second wavelength $\lambda_2$ onto the phosphor light source, and 2) direct light emitted by the phosphor toward the first dichroic optical element.

23. The illumination system of claim 22, further comprising:
 an optical filter between the third dichroic optical element and the first dichroic optical element, wherein the optical filter is configured to filter out a portion of light emitted by the phosphor light source.

24. The illumination system of claim 1, wherein directing the light emitted by the phosphor light source in the wavelength band $\Delta\lambda_{PHOSPHOR}$ to the optical output of the illumination system comprises transmitting the light emitted by the phosphor light source in the wavelength band $\Delta\lambda_{PHOSPHOR}$ to the optical output of the illumination system with the first dichroic optical element,
  wherein directing the light emitted by the third light source at the third wavelength $\lambda_3$ to the optical output of the illumination system comprises reflecting the light emitted by the third light source at the third wavelength $\lambda_3$ to the optical output of the illumination system with the first dichroic optical element,
  wherein directing the light emitted by the fourth light source at the fourth wavelength $\lambda_4$ to the optical output of the illumination system comprises reflecting the fourth light source at the fourth wavelength $\lambda_4$ to the optical output of the illumination system with the first dichroic optical element,
  wherein directing the light emitted by the third light source at the third wavelength $\lambda_3$ to the first dichroic optical element comprises transmitting the light emitted by the third light source at the third wavelength $\lambda_3$ to the first dichroic optical element with the second dichroic optical element, and
  wherein directing the light emitted by the fourth light source at the fourth wavelength $\lambda_4$ to the first dichroic optical element comprises reflecting the light emitted by the fourth light source at the fourth wavelength $\lambda_4$ to the first dichroic optical element with the second dichroic element.

25. The illumination system of claim 1, wherein the first wavelength $\lambda_1$ is between 440 nm and 490 nm and $\Delta\lambda_{PHOSPHOR}$ is between 500 nm and 750 nm.

26. The illumination system of claim 1, wherein the first wavelength $\lambda_1$ is between 445 nm and 475 nm and $\Delta\lambda_{PHOSPHOR}$ is between 530 nm and 630 nm.

27. The illumination system of claim 1, wherein $\Delta\lambda_{PHOSPHOR}$ is between 530 nm and 630 nm.

28. The illumination system of claim 1, wherein the second wavelength $\lambda_2$ is in a range selected from the group consisting of: 450 nm or less, 440 nm or less, and less than the first wavelength $\lambda_1$.

29. The illumination system of claim 1, wherein the first wavelength $\lambda_1$ is between 445 nm and 475 nm and the second wavelength $\lambda_2$ is 445 nm or less.

30. The illumination system of claim 1, wherein the third wavelength $\lambda_3$ is in the ultraviolet spectral region or the near ultraviolet spectral region.

31. The illumination system of claim 1, wherein each of the third wavelength $\lambda_3$ and the fourth wavelength $\lambda_4$ is in the near ultraviolet spectral region or the ultraviolet spectral region.

32. The illumination system of claim 1, wherein the second dichroic optical element has a band edge between the third wavelength $\lambda_3$ and the fourth wavelength $\lambda_4$.

33. An illumination system for fluorescence imaging and analysis, comprising:
  a light source module comprising:
    a first light source comprising a first light emitting device (LED) and a phosphor, the first LED for providing emission at a first wavelength $\lambda_1$ within an absorption band of the phosphor and the phosphor providing broadband light emission of longer wavelength comprising light in a wavelength band $\Delta\lambda_{PHOSPHOR}$; and
    a second light source for providing light at a second wavelength $\lambda_2$, within the absorption band of the phosphor;
  a controller for independently driving the first light source to generate emission at $\lambda_1$ and $\Delta\lambda_{PHOSPHOR}$ and driving the second light source and optically pumping the phosphor with the second wavelength $\lambda_2$, to increase emission in the emission band of the phosphor $\Delta\lambda_{PHOSPHOR}$;
  optical coupling means for coupling light emission to an optical output of the illumination system;
  another light source comprising an LED emitting at a third wavelength $\lambda_3$, wherein the optical coupling means comprises a first dichroic optical element having a band edge for reflecting the second wavelength $\lambda_2$ onto the phosphor for optical pumping of the phosphor, for transmitting emission from the first LED and the phosphor, comprising $\lambda_1$ and $\Delta\lambda_{PHOSPHOR}$, and further for reflecting the third wavelength $\lambda_3$, for optically coupling light emission, comprising $\lambda_1$, $\Delta\lambda_{PHOSPHOR}$ and $\lambda_3$, along a common optical axis to the optical output of the illumination system; and
  yet another light source emitting at a fourth wavelength $\lambda_4$ and wherein the optical coupling means further comprises a second dichroic element for coupling emission comprising $\lambda_3$ and $\lambda_4$, via the first dichroic element, along the common optical axis to the optical output of the illumination system, the second dichroic element having a band edge between $\lambda_3$ and $\lambda_4$.

34. The system of claim 33, wherein the second light source at the second wavelength $\lambda_2$ is a laser or an LED light.

* * * * *